United States Patent
Phan et al.

(10) Patent No.: US 10,799,125 B2
(45) Date of Patent: Oct. 13, 2020

(54) METHOD AND APPARATUS FOR MEASUREMENT OF CARDIOPULMONARY FUNCTION

(71) Applicants: Phi Anh Phan, Oxford (GB); Andrew Farmery, Oxford (GB); Clive Hahn, Radley (GB)

(72) Inventors: Phi Anh Phan, Oxford (GB); Andrew Farmery, Oxford (GB); Clive Hahn, Radley (GB)

( * ) Notice: Subject to any disclaimer, the term of this patent is extended or adjusted under 35 U.S.C. 154(b) by 115 days.

(21) Appl. No.: 15/129,171

(22) PCT Filed: Mar. 20, 2015

(86) PCT No.: PCT/GB2015/050830
§ 371 (c)(1),
(2) Date: Sep. 26, 2016

(87) PCT Pub. No.: WO2015/145115
PCT Pub. Date: Oct. 1, 2015

(65) Prior Publication Data
US 2017/0100043 A1  Apr. 13, 2017

(30) Foreign Application Priority Data
Mar. 24, 2014  (GB) .................................. 1405252.6

(51) Int. Cl.
*A61B 5/0205* (2006.01)
*A61B 5/08* (2006.01)
(Continued)

(52) U.S. Cl.
CPC .............. *A61B 5/0205* (2013.01); *A61B 5/08* (2013.01); *A61B 5/082* (2013.01); *A61B 5/7203* (2013.01);
(Continued)

(58) Field of Classification Search
CPC ............ A61M 16/0057; A61M 16/024; A61M 16/00; A61M 2205/3334; A61M 2230/40;
(Continued)

(56) References Cited

U.S. PATENT DOCUMENTS 6,131,571 A * 10/2000 Lampotang ........... A61M 16/00
                                                                          128/204.18
6,599,252 B2   7/2003 Starr
(Continued)

FOREIGN PATENT DOCUMENTS

| EP | 0653183 B1 | 1/1999 |
|----|------------|--------|
| EP | 1767235 A2 | 3/2007 |
| EP | 2311371 B1 | 11/2015 |

OTHER PUBLICATIONS

Clifton, L., Clifton, D. A., Hahn, C. E., & Farmery, A. D. (2013). Assessment of lung function using a non-invasive oscillating gas-forcing technique. Respiratory physiology & neurobiology, 189(1), 174-182.
(Continued)

*Primary Examiner* — Christian Jang
*Assistant Examiner* — Karen E Toth
(74) *Attorney, Agent, or Firm* — Troutman Pepper Hamilton Sanders LLP

(57) ABSTRACT

A method for measuring anatomical dead space in a lung, the method comprising: (a) providing, in a supply of inspired gas, at least one indicator gas for inhalation by a patient during a test, the concentration of the indicator gas being controlled such as to follow a sinewave pattern over successive breaths; (b) measuring, over successive breaths, the flow rate and concentration of the indicator gas during both inspiration and exhalation of the patient; (c) fitting sinewave envelopes to the measured concentration values of the indicator gas over the successive breaths and, from the fitted sinewave envelopes, determining the inspired concentration, (Continued)

the mixed expired concentration, and the end expired concentration in respect of the indicator gas for each breath; and (d) calculating the anatomical dead space for each of a plurality of inspirations based on a conservation-of-mass principle. Also provided is a test apparatus for carrying out such a method, and a computer program or set of instruction code which, when executed, causes a processor to implement such a method.

18 Claims, 14 Drawing Sheets

(51) Int. Cl.
    *A61B 5/00*     (2006.01)
    *A61B 5/087*     (2006.01)
    *A61B 5/091*     (2006.01)

(52) U.S. Cl.
    CPC .......... *A61B 5/7221* (2013.01); *A61B 5/7235* (2013.01); *A61B 5/087* (2013.01); *A61B 5/091* (2013.01)

(58) Field of Classification Search
    CPC . A61M 2016/003; A61M 16/022; A61B 5/08; A61B 5/087; A61B 5/082; A61B 5/4836; A61B 5/097; G01F 1/00
    See application file for complete search history.

(56) References Cited

U.S. PATENT DOCUMENTS

2009/0320844 A1     12/2009   Nielsen et al.
2011/0098589 A1     4/2011    Clemensen et al.

OTHER PUBLICATIONS

Clifton, L., Clifton, D. A., Hahn, C. E., & Farmeryy, A. D. (2013). A Non-Invasive Method for Estimating Cardiopulmonary Variables Using Breath-by-Breath Injection of Two Tracer Gases. IEEE journal of translational engineering in health and medicine, 1, 1-8.
Hahn, C. E. W., & Farmery, A. D. (2003). Gas exchange modelling: no more gills, please. British journal of anaesthesia, 91(1), 2-15.
Huber, P. J., & Ronchetti, E. M. (2009). Robust Statistics. Hoboken. NJ: Wiley. doi, 10(1002), p. 152-165.
International Preliminary Report on Patentability issued by the International Bureau of WIPO, Application No. PCT/GB2015/050830, dated Sep. 27, 2016, 8 pages.
International Search Report and Written Opinion of the International Searching Authority, Application No. PCT/GB2015/050830, dated Jun. 1, 2015, 10 pages.
Quanjer, P. H., Tammeling, G. J., Cotes, J. E., Pedersen, O. F., Peslin, R., & Yernault, J. C. (1993). Lung volumes and forced ventilatory flows. Report Working Party Standardization of Lung Function Tests, European Community for Steel and Coal. Official Statement of the European Respiratory Society. European Respiratory Journal, 6(Suppl 16), 5-40.
Tang, Y., Turner, M. J., & Baker, A. B. (2006). A new equal area method to calculate and represent physiologic, anatomical, and alveolar dead spaces. The Journal of the American Society of Anesthesiologists, 104(4), 696-700.
Weismann, D., Reißmann, H., Maisch, S., Füllekrug, B., & Schulte, J. (2006). Monitoring of functional residual capacity by an oxygen washin/washout; technical description and evaluation. Journal of clinical monitoring and computing, 20 (4), 251-260.
West J.B. 2008 Respiratory Physiology: the Essentials. Lippincott Williams & Wilkins, p. 17-19.
Communication pursuant to Article 94(3) EPC issued by the European Patent Office in connection with European Application No. 15713568.2, dated Nov. 10, 2017.
Examination Report issued by the European Patent Office in connection with European Application No. 15713568.2, dated Jul. 13, 2018.

* cited by examiner

METHOD AND APPARATUS FOR MEASUREMENT OF CARDIOPULMONARY FUNCTION

FIELD OF THE INVENTION

The present invention relates to a method and associated apparatus for non-invasively measuring aspects of cardiopulmonary function in a subject. For example, embodiments of the invention may be used for non-invasively measuring one or more of anatomical dead space, functional residual capacity (FRC), pulmonary blood flow, and lung inhomogeneity.

BACKGROUND TO THE INVENTION

Dead space, functional residual capacity, pulmonary blood flow, and lung inhomogeneity are important parameters in relation to the cardiopulmonary condition of a patient. While there are methods available using respired gases to measure these parameters individually, it is currently difficult or even impossible to simultaneously give measurements of dead space, FRC, pulmonary blood flow, and lung inhomogeneity, and to make these measurements continuously.

Dead space is the volume of air which is inhaled that does not take part in the gas exchange, either because it remains in the conducting airways, or reaches alveoli that are not perfused. Dead space is often measured using the Bohr equation for physiological dead space, or Fowler's method for anatomical dead space. U.S. Pat. No. 6,599,252 (Starr, 2003) describes a method and apparatus to determine anatomical dead space using a sensor indicating volume and a gas analyser measuring concentration of a gas such as $CO_2$ or $O_2$ in a patient's expiratory flow.

Functional residual capacity (FRC) is the volume of gas, including carbon dioxide, remaining within the lungs of a subject at the end of passive expiration. Common methods to measure FRC include body plethysmography, helium dilution, and gas wash-in/wash-out techniques. Such methods are described in the literature (West, 2008) and in EP 0653183 (Larsson et al., 1999) and EP 1767235 (Choncholas et al., 2007), which describe adaptations of gas wash-in/wash-out techniques for used in ventilated patients.

Pulmonary blood flow is the average total blood flow per unit time in pulmonary circulation. For non-invasive pulmonary blood flow measurement using respired gases, a variety of indirect Fick techniques including single breath and rebreathing have been proposed over the years. Only a few techniques are commercially available, such as the Novametrix Non-Invasive Cardiac Output (NICO) which uses $CO_2$ rebreathing technique, or the Innocor technique (US 2009/0320844 (Clemensen and Nielsen, 2009) and US 2011/0098589 (Clemensen and Nielsen, 2011) which uses $N_2O$ rebreathing. However, a major disadvantage of rebreathing techniques is that it requires a bag system and therefore cannot be used for ventilated patients.

It is unfortunate that ventilated patients, who are the most in need of monitoring cardiopulmonary function, are the hardest group to test using traditional methods. The information regarding the cardiopulmonary function is not only important to monitor how the ventilated patients recover over time, but is also useful to help choose appropriate ventilator settings such as tidal volume and the positive end expiratory pressure (PEEP).

Lung inhomogeneity is another important parameter. However at present, only the lung clearance index, which is derived from a washout test, is an accepted technique to investigate ventilation-volume inhomogeneity.

No established technique exists to investigate ventilation-perfusion inhomogeneity using respired gases. No established technique exists to combine the above-described methods to provide simultaneous information on dead space, FRC, pulmonary blood flow, and lung inhomogeneity. It is possible that the re-breathing techniques of others as described above might be adaptable to measure FRC and pulmonary blood flow, using an inert insoluble gas. The limitations of such a theoretical procedure however include the fact that it would not be possible to use for ventilated patients.

There is accordingly a need for a method which will accurately provide measurements of one or more of dead space, FRC, pulmonary blood flow, and lung inhomogeneity. There is a need for a method which can be used to provide such measurements for a ventilated patient. There is a need for a method which can be used non-invasively to provide such measurements and for these measurements to be made continuously.

SUMMARY OF THE INVENTION

The present invention addresses one or more of the above needs by providing an apparatus and method which permit the simultaneous measurement of the above cardiopulmonary parameters (dead space, FRC, pulmonary blood flow, and lung inhomogeneity) and that can also be applied to a ventilated patient. The method and apparatus of the present invention can be used for other patient groups such as neonates and elderly patients, or other patient groups who cannot co-operate easily with clinicians, such as the obese (who cannot be put in a body plethysmography).

The invention is based upon the inspired sinewave technique, which differs from the above-mentioned techniques of rebreathing and wash-in/wash-out in that concentration of an inspired gas is forced to follow a sinewave pattern. The expired concentration of the same gas will also follow a sinewave pattern.

The use of the inspired sinewave technique has been previously investigated, but resulted in significant errors leading to incorrect results and a technique that could not be used clinically. In particular, because of hardware limitations and rudimentary analytical techniques, the dead space recovered was over-estimated, which then resulted in an under-estimation of the FRC and pulmonary blood flow: estimated blood flow was 3 L/min compared to the expected 5.6 L/min for a male and 4.9 L/min for a female (Clifton et al., 2013 (two references)). Steps to address robustness and outliers were also not described, which further added to the inaccuracy and low repeatability of the estimation of the FRC and pulmonary blood flow. Table 1 below shows the over-estimation of dead space using this previous method, in three different setups of a mechanical bench lung with known dead space.

The present inventors have determined that these failings were based on not taking into account the non-uniform variation of inspired concentrations in both the determination of dead space and the determination of functional residual capacity and pulmonary blood flow. Accordingly, it was not possible to use the technique to provide a measurement of lung inhomogeneity. The present invention focuses on eliminating such inaccuracy by the techniques described herein, thus providing an apparatus and method to implement the inspired sinewave technique in a clinical setting (such as a bedside setting or in an intensive care unit) or on ventilated patients. The present invention provides a method that can be used to accurately measure cardiopulmonary parameters and provide a measurement of lung inhomogeneity.

Thus, according to a first aspect of the invention there is provided a method for measuring anatomical dead space $V_D$ in a lung, the method comprising:
(a) providing, in a supply of inspired gas, at least one indicator gas for inhalation by a patient during a test, the concentration of the indicator gas being controlled such as to follow a sinewave pattern over successive breaths;
(b) measuring, over successive breaths, the flow rate and concentration of the indicator gas during both inspiration and exhalation of the patient;
(c) fitting sinewave envelopes to the measured concentration values of the indicator gas over the successive breaths and, from the fitted sinewave envelopes, determining the inspired concentration $F_I$, the mixed expired concentration $F_{\bar{E}}$, and the end expired concentration $F_E$ in respect of the indicator gas for each breath; and
(d) calculating the anatomical dead space $V_D$ for each of a plurality of inspirations, by:
  (i) calculating the tidal volume $V_T$ for the given inspiration by integrating over time, from the start of that inspiration, the flow rate $\dot{V}_T(t)$ of the inspired gas for that inspiration;
  (ii) calculating the volume of inspired indicator gas in the given inspiration by integrating over time, from the start of that inspiration, the product of the inspired concentration $F_I$ and the flow rate $\dot{V}_T(t)$ of inspired gas for that inspiration; and
  (iii) calculating the dead space $V_D$ for the given inspiration, based on:
    the tidal volume $V_T$ for that inspiration;
    the inspired concentration $F_I$ of indicator gas for that inspiration;
    the mixed expired concentration $F_{\bar{E}}$ of indicator gas for that inspiration; and
    the alveolar gas concentration $F_A$ for that inspiration, which is taken as the expired concentration $F_E$ of indicator gas at the end of that expiration;
    the calculating involving a conservation-of-mass principle during expiration, between the amount of indicator gas expired out and the sum of the amount of indicator gas remaining in the deadspace and the amount of indicator gas expired from the part of the lung where gas exchange has taken place, whereby, having determined the inspired concentration $F_I$, the flow rate $\dot{V}_T(t)$, the tidal volume $V_T$, the mixed expired concentration $F_{\bar{E}}$, and the alveolar gas concentration $F_A$, a mass balance equation is solved to give an estimation of the dead space $V_D$ for each breath.

An advantage of this method over methods based on the Bohr method described above is that the Bohr method assumes that inspired concentration of the inert gas is uniform and constant. The present inventors have found that the concentration of the inspired inert gas is non-uniform and thus that estimation methods based on assuming a uniform concentration will lead to significant error. The method of the present invention accommodates non-uniform concentration and thus provides an accurate measurement of anatomical dead space within a lung. By way of example, Table 1 below shows that the estimation of dead space by an embodiment of the present invention out-performs (i.e. is more accurate than) the estimation by the previous method (Clifton et al., 2013 (two references)), in three setups of a laboratory mechanical bench lung with known dead space.

This accurate measurement of anatomical dead space permits the accurate measurement of other lung parameters, such as functional residual capacity, pulmonary blood flow and lung inhomogeneity as will be discussed further below.

Preferably, in providing the at least one indicator gas for inhalation, the concentration of the indicator gas is controlled such as to follow a sinewave pattern over successive breaths by:
  providing flow control means for injecting the indicator gas into the supply of inspired gas;
  processing the measured flow rate and concentration of the inspired indicator gas over each breath so as to determine, from breath to breath, an injection rate for the inspired indicator gas that will cause it to follow the sinewave pattern, and
  providing feedback control to the flow control means, to cause it to inject the indicator gas at the determined injection rate.

In some embodiments, part of the supply of inspired gas is taken from ambient air. In other embodiments, part of the supply of inspired gas is provided by a ventilator.

Preferably the tidal volume $V_T$ for each of the plurality of inspirations is calculated using $\int_{t_{insp}} \dot{V}_T(t) \times dt$, where $t_{insp}$ is the time at the start of inspiration and $\dot{V}_T(t)$ is the inspired flow rate.

Preferably the dead space $V_D$ for each of the plurality of inspirations is calculated using an algorithm to solve $f(V_D) - F_A \times V_D = (F_{\bar{E}} - F_A) \times V_T$, where $F_A$ is the alveolar gas concentration, $F_{\bar{E}}$ is the mixed expired concentration and $V_T$ is the tidal volume.

Preferably the method further comprises applying an estimation method to the calculated anatomical dead space values for the plurality of inspirations, in order to remove outliers and obtain a final dead space value $\hat{V}_{D,final}$.

Preferably the estimation method is a robust estimation method, such as an M-estimator proposed by (Huber and Ronchetti, 2009):

$$\hat{V}_{D,final} = \underset{\theta}{\operatorname{argmin}} \left( \sum_{n=1}^{n\_total} \rho(V_{D,n}, \theta) \right)$$

in which $\theta$ is the parameter to estimate the final dead space value, $V_{D,n}$ is the dead space value estimated for an n-th breath, $\rho(V_{D,n},\theta)$ is the Huber loss function:

$$\rho(V_{D,n}, \theta) = \begin{cases} \frac{1}{2}(V_{D,n} - \theta)^2 & \text{for } |V_{D,n} - \theta| < k \\ k|V_{D,n} - \theta| - \frac{1}{2}k^2 & \text{for } |V_{D,n} - \theta| \geq k \end{cases},$$

and k is a constant chosen based on the quality of the data. It should be noted that the invention is not limited to this particular M-estimator; more sophisticated robust methods can also be used to remove outliers and improve the estimation of the final value of dead space.

Preferably the robust estimation method provides a 95% confidence interval.

The method of the present invention may also include measuring one or more of functional residual capacity, pulmonary blood flow and lung inhomogeneity.

One or both of the alveolar volume $V_A$ and the pulmonary blood flow $\dot{Q}_P$ may be estimated as slopes of a virtual 3D surface $V_A \times x + \dot{Q}_P \times y = z$, where $$x_n = F_{A,n} - F_{A,n-1}$$

$$y_n = \lambda \times (F_{A,n} - \overline{F}_A) \times \Delta t_n;$$

$$z_n = V_D \times (F_{\overline{I},n} - F_{A,n-1}) + V_{T,n} \times (F_{A,n} - F_{\overline{I},n})$$

in which $V_D$ is the dead space volume, $V_{T,n}$ is the tidal volume of an n-th breath, $\lambda$ is the solubility of the indicator gas, $\Delta t_n$ is the respiration time of the n-th breath, $F_{A,n}$ is the alveolar concentration of the n-th breath, $F_v$ is the concentration of the mixed venous sinewave, and $F_{\overline{I A},n}$ is the mixed inspired concentration of the indicator gas as 'seen' by the alveolar compartment.

An advantage of this 3D surface approach is that it allows a robust estimation method (such as bisquare) to be used to remove outliers and to provide a confidence interval (e.g. a 95% confidence interval).

Thus, the method may further comprise steps such as maximum likelihood techniques to remove outliers from the estimated values of the alveolar volume $V_A$ and/or pulmonary blood flow $\dot{Q}_P$, so as to give robust estimations of the alveolar volume $V_A$ and/or pulmonary blood flow $\dot{Q}_P$, and corresponding confidence intervals (e.g. 95% confidence intervals).

The method may further comprise calculating the functional residual capacity as the sum of the alveolar volume $V_A$ and the dead space $V_D$.

Preferably the data used for the calculation of the alveolar volume $V_A$ and/or the pulmonary blood flow $\dot{Q}_P$ are obtained using a sinewave period in the range of 0.5 minutes to 5 minutes—particularly preferably using a sinewave period of approximately 3 minutes.

To obtain a measurement of lung inhomogeneity, the method may further comprise:
  varying the period of the sinewave during the course of the test;
  determining, at different sinewave periods, values of one or more of the dead space $V_D$, alveolar volume $V_A$, functional residual capacity, and pulmonary blood flow $\dot{Q}_P$; and
  providing a measurement of lung inhomogeneity based on the variation in the determined values with sinewave period.

For example, the period of the sinewave may be varied across the range of 0.5 minutes to 5 minutes. Of these, periods in the range of 2 minutes to 4 minutes may advantageously be used to determine inhomogeneity in respect of one or more of the alveolar volume $V_A$, functional residual capacity, and pulmonary blood flow $\dot{Q}_P$.

The method may further comprise evaluating one or more of the following indices $I_1$, $I_2$, $I_3$ and $I_4$, wherein:

$$I_1 = \frac{V_A(4 \text{ mins}) - V_A(0.5 \text{ mins})}{V_A(0.5 \text{ mins})},$$

$$I_2 = \frac{V_{A,predict}}{V_A(0.5 \text{ mins})},$$

$$I_3 = \frac{V_{A,plethysmograph}}{V_A(0.5 \text{ mins})}, \text{ and}$$

$$I_4 = \frac{\dot{Q}_P(2 \text{ mins}) - \dot{Q}_P(4 \text{ mins})}{\dot{Q}_P(4 \text{ mins})};$$

in which $V_A(0.5 \text{ mins})$ and $V_A(4 \text{ mins})$ are the lung volume estimated at sinewave periods of 0.5 minutes and 4 minutes respectively; $\dot{Q}_P(2 \text{ mins})$ and $\dot{Q}_P(4 \text{ mins})$ are the pulmonary blood flow estimated at sinewave periods of 2 minutes and 4 minutes respectively, $V_{A,plethysmograph}$ is the lung volume measured by body plethysmography, and $V_{A,predict}$ is the predicted lung volume calculated from the height and weight of the subject.

The indicator gas may be nitrogen, nitrous oxide or oxygen. Additionally or alternatively, other inert gases such as argon may be used as the indicator gas.

If desired, in practical implementations, at least one of the fitting of the sinewave envelopes to the measured concentration values, and the calculating, may be performed after the test has been carried out optionally without the patient being present. Alternatively the fitting of the sinewave envelopes to the measured concentration values, and the calculating, may be performed in an ongoing manner, at periodic intervals, with the patient present, in order to provide continuous monitoring of the patient.

According to a second aspect of the invention there is provided a method for measuring anatomical dead space in a lung, the method comprising:
  (a) providing, in a supply of inspired gas, at least one indicator gas for inhalation by a patient during a test, the concentration of the indicator gas being controlled such as to follow a sinewave pattern over successive breaths;
  (b) measuring, over successive breaths, the flow rate and concentration of the indicator gas during both inspiration and exhalation of the patient;
  (c) fitting sinewave envelopes to the measured concentration values of the indicator gas over the successive breaths and, from the fitted sinewave envelopes, determining the inspired concentration, the mixed expired concentration, and the end expired concentration in respect of the indicator gas for each breath; and
  (d) calculating the anatomical dead space for each of a plurality of inspirations based on a conservation-of-mass principle.

The above-described "preferable" or optional features in relation to the first aspect of the invention are also applicable to the second aspect of the invention.

According to a third aspect of the invention there is provided test apparatus configured for carrying out the above-described methods of the first and second aspects of the invention.

Preferably the apparatus comprises one or more mass flow controllers as means for injecting the indicator gas(es) into the supply of inspired gas.

Preferably the apparatus comprises a diffusing injector for injecting the indicator gas(es) into the supply of inspired gas.

Preferably the apparatus comprises a real-time flow rate sensor as means for measuring the flow rate of the inspired and expired gases.

Preferably the apparatus comprises a mainstream gas analyser as means for measuring the concentration of the indicator gas(es) during inspiration and exhalation.

Preferably the apparatus comprises a processor provided with instruction code which, when executed, causes the processor to control the mixing of the indicator gas with the other inspired gas(es) according to the breathing flow of the patient, so that the concentration of the indicator gas follows a sinewave pattern over successive breaths.

Preferably the instruction code, when executed, provides a user with control means operable to adjust one or more of the magnitude, phase, means and period of the indicator gas(es) delivered to the patient.

Particularly preferably the control means are operable to make the adjustment(s) in real time.

Preferably the apparatus comprises a processor provided with instruction code which, when executed, causes the processor to record the measured flow rate and concentration of the indicator gas(es) during inspiration and exhalation of the patient. This processor may be the same as the processor mentioned above, or may be a different processor.

Preferably the apparatus further comprises display means configured to display the flow and concentration of the indicator gas(es) in real time.

The instruction code, when executed, may further cause the processor to calculate one or more of the anatomical dead space $V_D$, the alveolar volume $V_A$, the pulmonary blood flow $\dot{Q}_P$ and the functional residual capacity, optionally together with 95% confidence intervals, and these results may be displayed on the display means.

The test apparatus may further comprise one or more indicator gas supplies, e.g. in the form of gas canisters.

The test apparatus may be in the form of a portable unit. For example, it may be wheel-mounted in trolley-like form, for use for example in a clinical environment such as by a patient's bedside or in an operating theatre or intensive care unit.

Alternatively the test apparatus may be incorporated in a ventilator.

Thus, a further aspect of the invention provides a ventilator comprising test apparatus in accordance with the second aspect of the invention.

According to a yet further aspect of the invention there is provided a computer program or set of instruction code which, when executed, causes a processor to implement a method in accordance with the first aspect of the invention.

BRIEF DESCRIPTION OF THE DRAWINGS

Embodiments of the invention will now be described, by way of example only, and with reference to the drawings in which.

DETAILED DESCRIPTION OF PREFERRED EMBODIMENTS

Overview of the Inspired Sinewave Device

Figure 1:
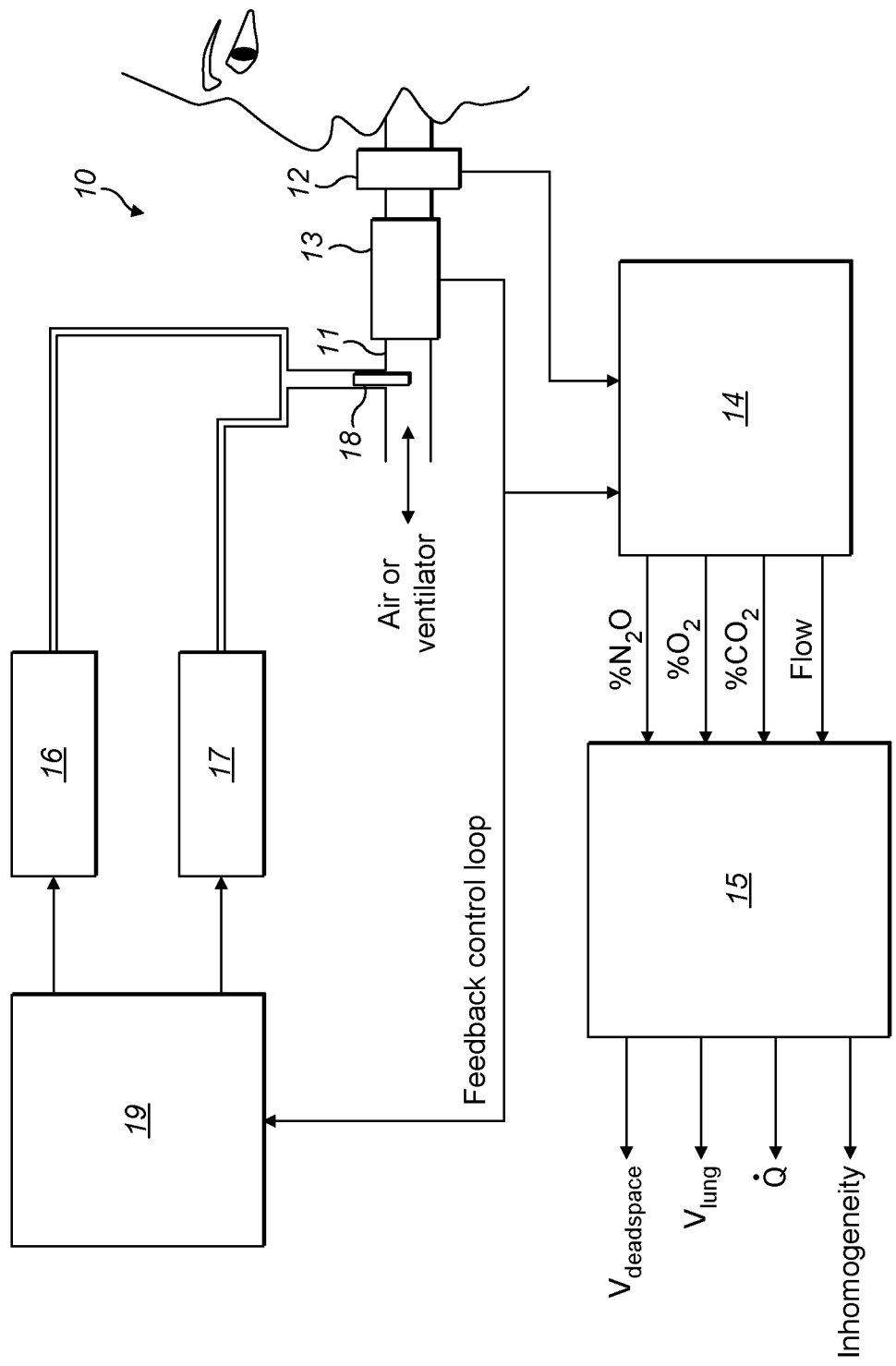
FIG. 1 shows a schematic diagram illustrating a setup for the inspired sinewave test, according to an embodiment of the invention.

With reference to the figures, FIG. 1 provides an overview of the functional arrangement of an inspired sinewave device 10 according to an embodiment of the invention.

As illustrated, the inspired sinewave device 10 comprises a breathing tube 11, a mainstream gas analyser 12, a flow sensor 13, a data acquisition unit 14, a processing unit 15 configured to implement analysing algorithms, a $N_2O$ mass flow controller 16, an $O_2$ mass flow controller 17, a mixing nozzle 18, and a controller 19.

In use, the patient breaths through the breathing tube 11 either by a mouthpiece or a face mask. The other end of breathing tube 11 is either connected to air (for spontaneous breathing patients) or to a ventilator (for ventilated patients). On this breathing tube 11, the mainstream gas analyser 12 is mounted to measure the concentration of $N_2O$, and potentially of $O_2$ and $CO_2$ too. For example, infrared sensors can be used to measure $N_2O$ and $CO_2$ concentrations. For measuring $O_2$ concentration, a fuel cell sensor can be used. Also on this breathing tube 11, flow sensor 13 is attached to measure the flow rate as accurately as possible in real time. For example, an ultrasound flow sensor can be used to measure the flow rate. The signals from the gas analyser 12 and flow sensor 13 are acquired and processed by the data acquisition unit 14, before feeding into the processing unit 15 which implements analysis algorithms on the acquired signals. The analysis algorithms perform the necessary calculation steps to give robust and accurate estimations of the cardiopulmonary parameters. Details of these steps will be described later.

A key aspect of embodiments of the invention is to have the concentrations of the inspired indicator gases follow sinusoidal patterns, and this is achieved using feedback control by the gas mixing apparatus (16, 17, 18, 19) also shown in FIG. 1. The gas mixing apparatus includes high speed $N_2O$ and $O_2$ mass flow controllers 16 and 17 respectively, to inject $N_2O$ and $O_2$ into the breathing tube 11. During inspirations, the gases in the breathing tube 11 is a mixture of inlet gas (either air or from a ventilator), injected $N_2O$ and injected $O_2$, to create the desired $N_2O$ and $O_2$ concentrations.

At the start of each inspiration, the desired concentrations are determined as the values of the inspired sinusoidal waveforms at that point in time. By measuring the real time flow rate using the flow sensor 13, the controller 19 computes the desired injection rates according to the instantaneous breathing rate of the patient and the desired concentrations. The controller 19 then sends commands to mass flow controllers 16 and 17 to inject the required amount of $N_2O$ and $O_2$ into the breathing tube 11 through the mixing nozzle 18. The mixing nozzle 18 diffuses the injected $N_2O$ and $O_2$ evenly in the breathing tube 18 to create the mixture of gases with the desired concentrations, which is then inhaled by the patients. The formulae and algorithm implemented by controller 19 to determine the desired injection rates from the flow rate and inspired sinusoidal waveforms will be described later. Even though a system of two mass flow controllers 16, 17 for $N_2O$ and $O_2$ is demonstrated here, it is easy to extend this system to include more mass flow controllers if more sinewaves of gases are required. For example, a mass flow controller for argon could be added to generate an inspired sinewave of argon.

Another aspect of embodiments of the invention is to integrate flow and concentration signals to obtain the amounts of gases inspired/expired during the test. Signal synchronisation has been a problem for mass spectrometers and side-stream gas analysers. As samples of gases need to be sucked out of the breathing tube, side-stream gas analysers have a long and varying time delay that can cause errors in integration. Methods have been developed to address this signal synchronisation problem, such as one used by the LUFU system (Draeger Medical; LObeck, Germany) that synchronises flow and $FiO_2$ (fraction of inspired oxygen) signals while adjusting for gas viscosity (Weismann et al., 2006). For the present embodiments, a mainstream gas analyser 12 is used and therefore eliminates the problem of long time delay between signals. The mainstream gas analyser 12 can be of any technology available for mainstream sensing such as infrared for $CO_2$ and $N_2O$, fuel cell for $O_2$, and optical laser for $O_2$, $CO_2$ and $N_2O$. As shown in FIG. 1, the main gas analyser 12 is mounted directly onto the breathing tube 11, and in series with the flow sensor 13, allowing straightforward integration. With this setup, the time delay has been determined experimentally as being less than 10 ms, and can be corrected straightforwardly in the software.

The device also includes a controller 19 (that may be, for example, microprocessor-controlled or computer-controlled) to control the mass flow controllers 16, 17, record sensor data, and analyse test results in real time. As part of embodiments of the invention, the computer controller 19 used by the device has a graphical user interface designed specifically to facilitate the administering of the inspired sinewave technique in a clinical environment, such as by the patient's bedside or in an operating theatre or intensive care unit.

Figure 2A:
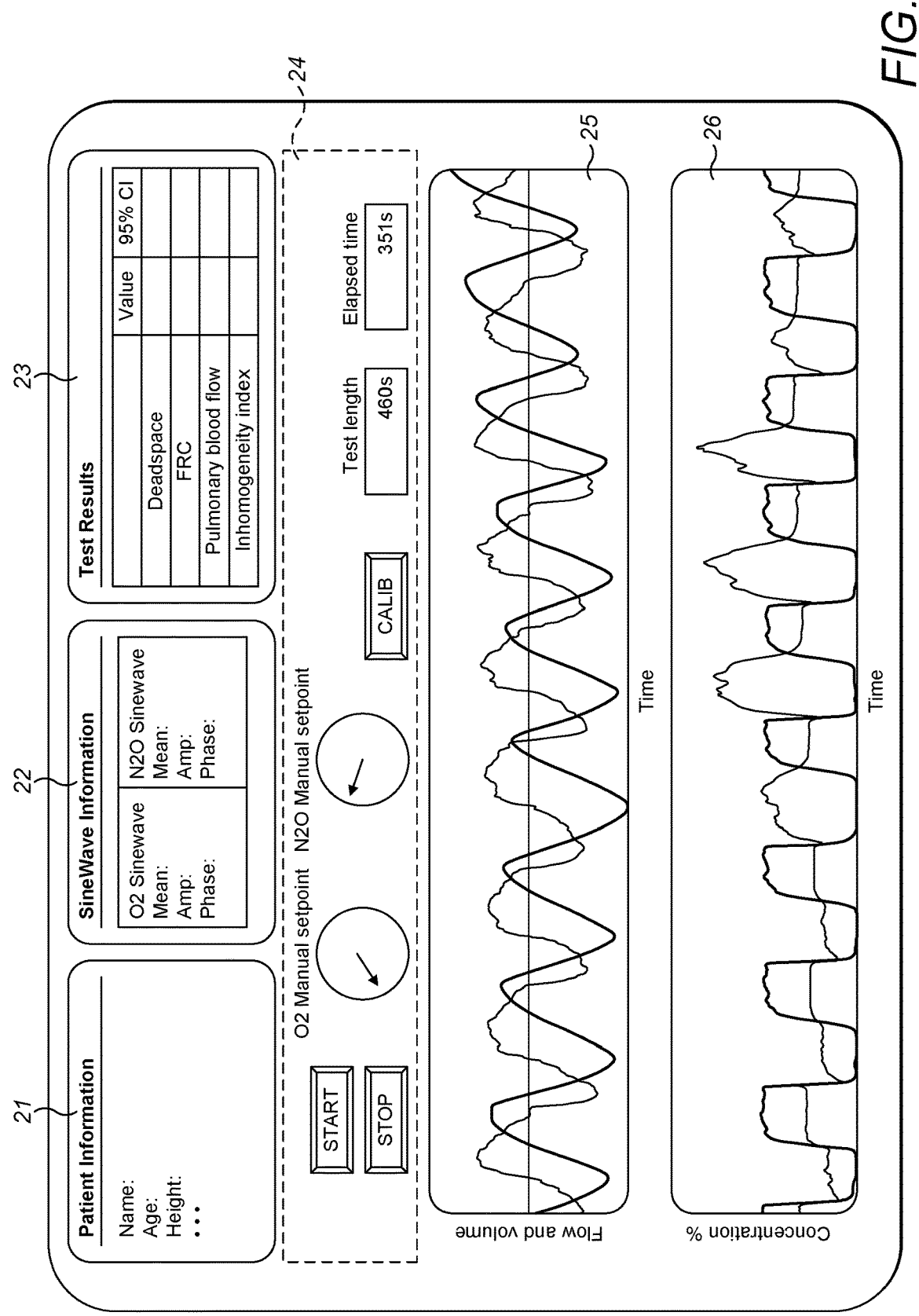
FIG. 2a is a schematic illustration of a graphical user interface according to an embodiment of the invention, showing (i) displays of signals in real time, (ii) control panels, and (iii) displays of test results.
Figure 2B:
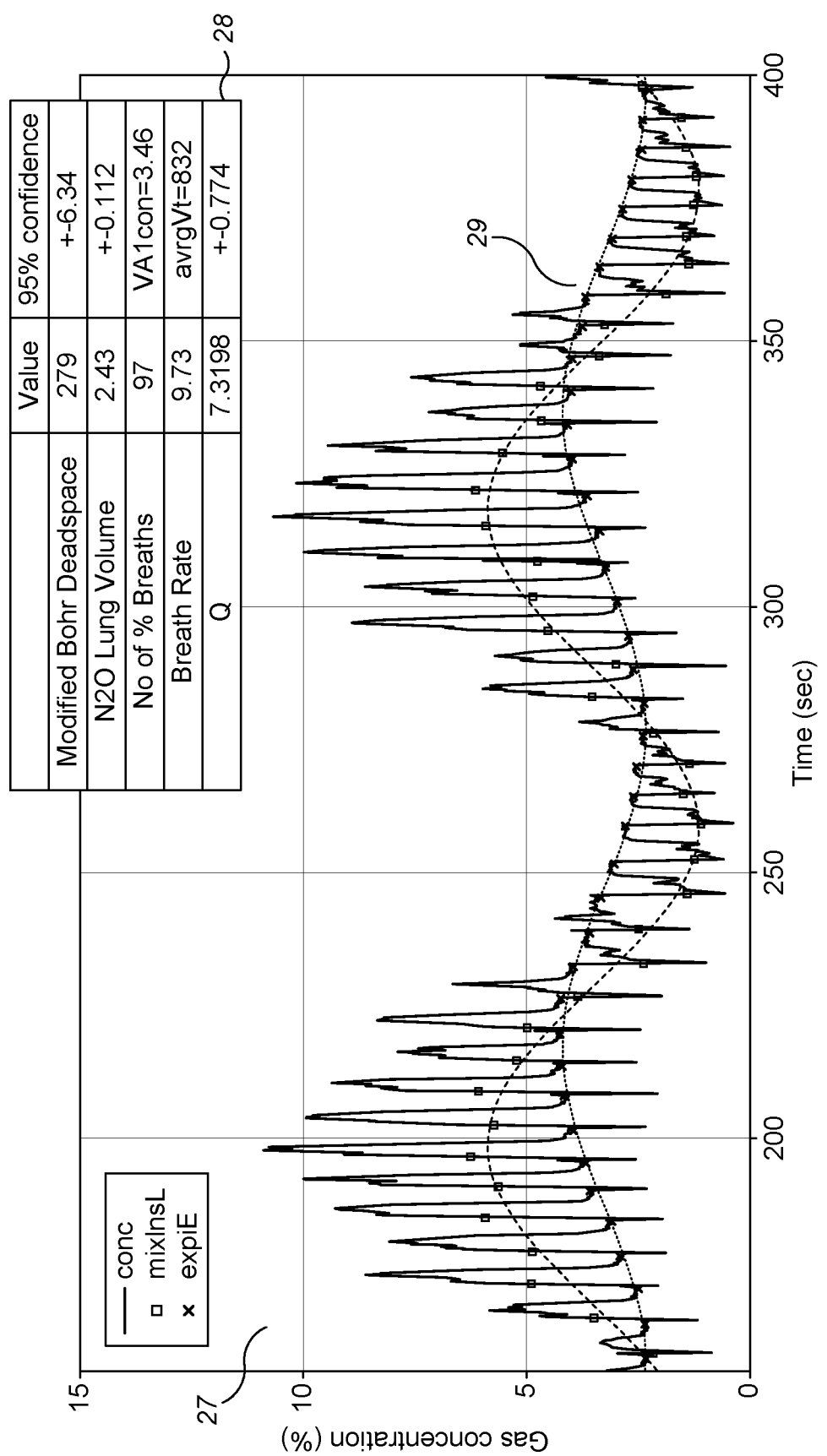
FIG. 2b depicts a pop-up screen within the graphical user interface, allowing more detailed analysis of the test results.

Towards this objective, as shown in FIG. 2a, the graphical user interface includes table 21 for entering patient information (e.g. name, age, height, weight, etc.), table 22 for entering sinewave parameters (e.g. mean, amplitude and phase of $O_2$ sinewave; and mean, amplitude and phase of $N_2O$ sinewave), table 23 for displaying test results, control panel 24 for controlling the sinewave test, display 25 for displaying real time flow and volume signals, and display 26 for displaying real time concentrations of gases. Table 23 includes both values and 95% confidence intervals of estimated dead space, FRC, pulmonary blood flow, and lung inhomogeneity. Control panel 24 includes START, STOP and CALIBARATION ("CALIB") buttons, and also dials for manual control of inspired gas concentrations. Once a sinewave test completes, a pop-up screen 27 (FIG. 2b) with cursors also allows more detailed analysis of results within the graphical user interface. Table 28 and waveforms 29 respectively show the more detailed results and sinewave data within pop-up screen 27.

The software and processing algorithms used in the present embodiments may be provided as a computer program or set of instruction code capable of being executed by a computer processor. The computer processor may be that of a conventional (sufficiently high performance) computer, or may be an application-specific processor. The computer processor may provided in a computing device separate from, but in communication with, the test apparatus; or may be incorporated in the test apparatus itself.

The computer program or set of instruction code may be supplied on a computer-readable medium or data carrier such as a CD-ROM, DVD or solid state memory device. Alternatively, it may be downloadable as a digital signal from a connected computer, or over a local area network or a wide area network such as the Internet. As a further alternative, the computer program or set of instruction code may be hard-coded in the computer processor (or memory associated therewith) that is to execute it.

Figure 3:
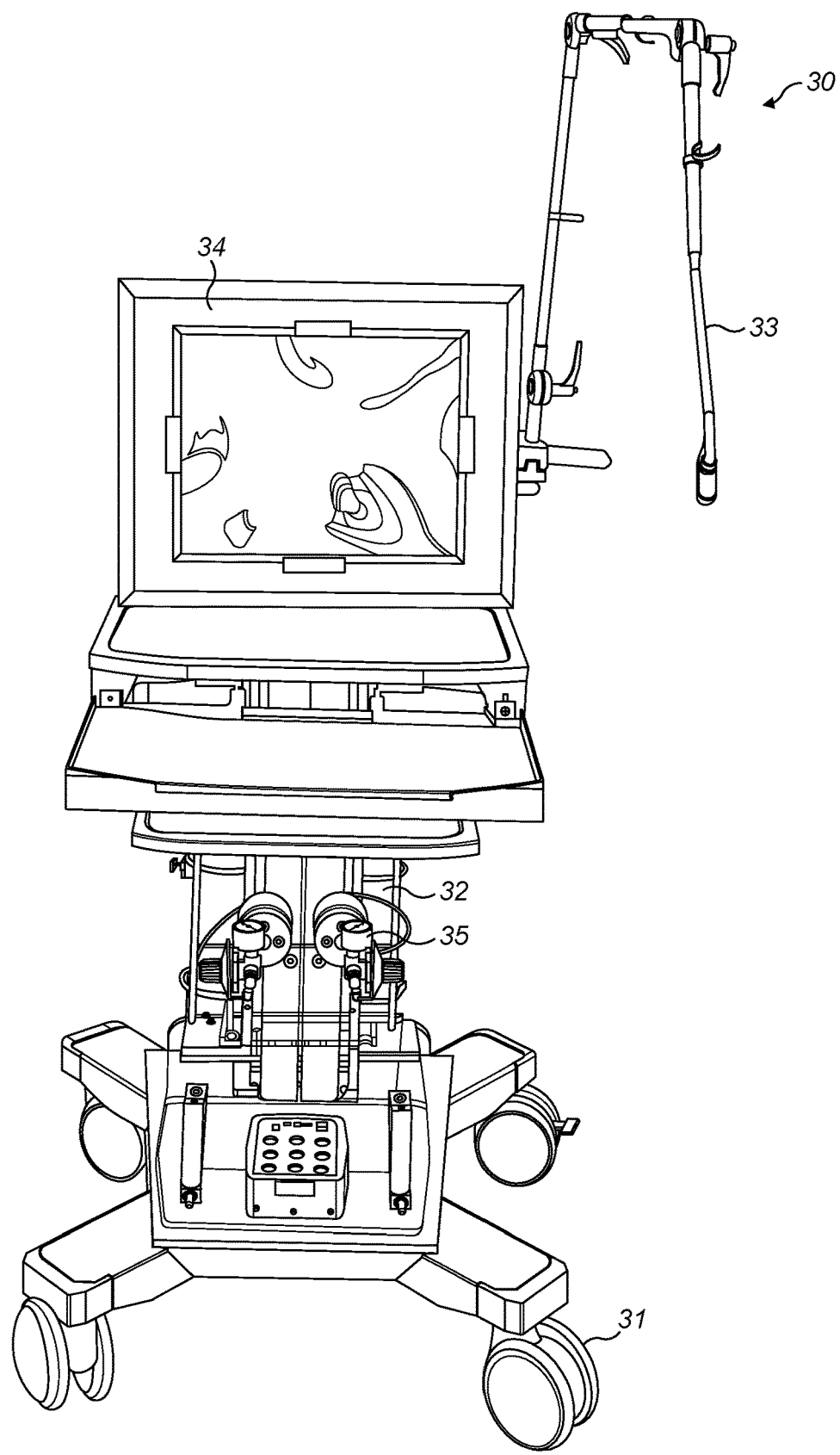
FIG. 3 shows an example setup of an embodiment of the invention, for standalone and mobile use in clinical environments (this representing only one possible way in which the invention can be embodied; another option, for example, is to incorporate the invention into a ventilator as a module)

FIG. 3 shows a prototype hardware setup of an embodiment of the invention, for ease of use by the patient's bedside, e.g. in an operating theatre or intensive care unit. The whole system 30 is mounted on wheels and brakes 31 for mobile use, i.e. in the form of a trolley. Gas cylinders 32 supplying the required gases are also mounted on the trolley. An articulated arm 33 is attached to hold the breathing tube 11 (of FIG. 1), which also includes the gas mixing apparatus, flow sensor 13, and gas analyser 12. A computer and display 34, preferably touch screen type, is used to control the test, and analyse and display results. The pressure and flow control hardware 35 for the gas mixing apparatus is kept on shelves mounted on the trolley. This only shows one possible setup of an embodiment of the invention, and does not limit the invention in any way. Those skilled in the art will be able to suggest many alternative setups of implementation without departing from the scope of the appended claims. For example, another possible setup is a smaller unit which can be incorporated into a ventilator as a module.

Figure 4:
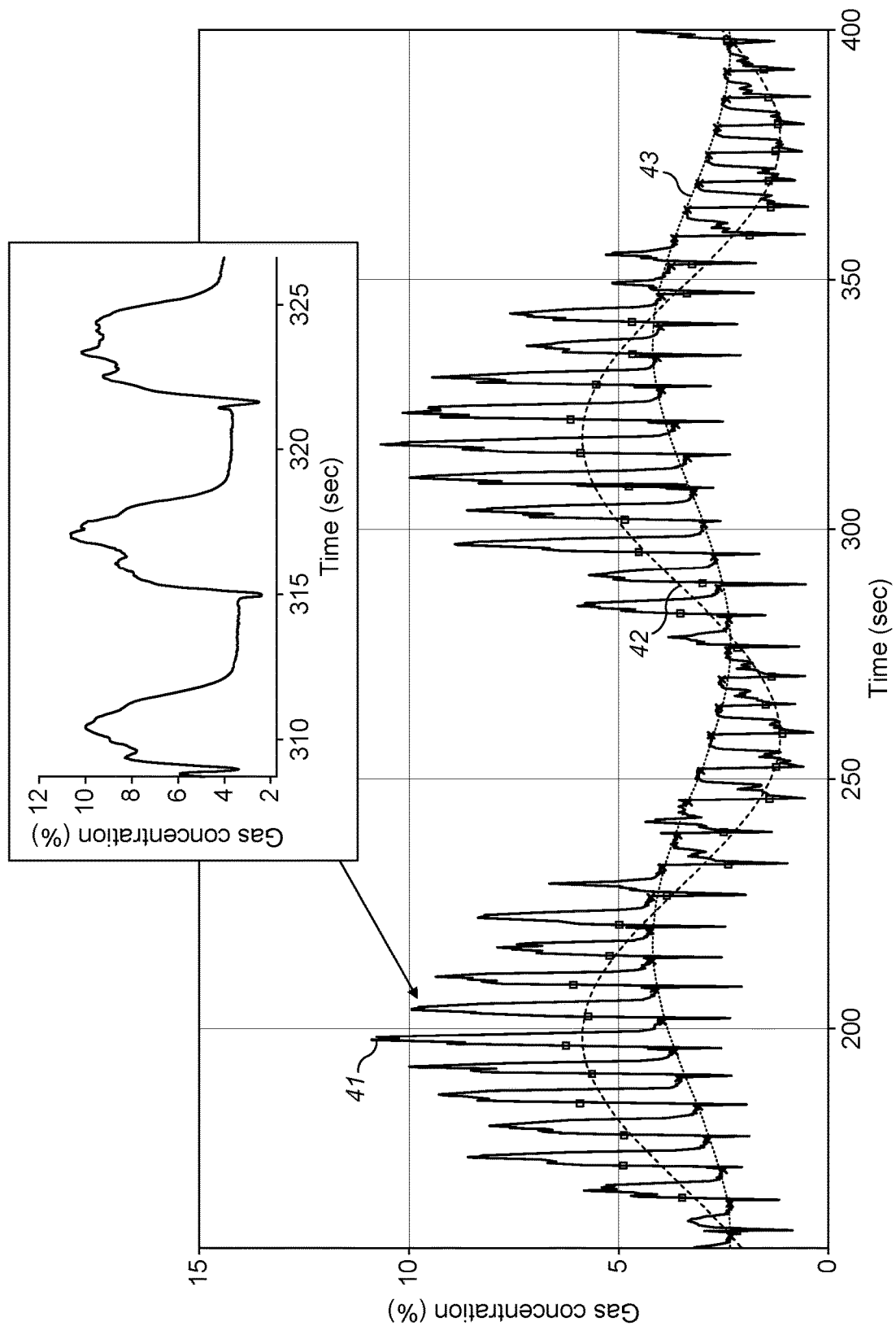
FIG. 4 shows an example of the concentration signal in an inspired sinewave test.

FIG. 4 demonstrates an example of the concentration generated and measured in an inspired sinewave test, and also how the sinewaves are determined. Line 41 shows the concentration signal measured by the gas analyzer 12 (of FIG. 1). On a closer look, this signal contains two components (sinewave envelopes): inspired concentration corresponding to the inspiration phase, and expired concentration corresponding to the expiration phase. By calculating the mixed inspired and mixed expired concentrations for each breath, a series of inspired and expired concentration points are generated as shown respectively by □ and x points on the plot. By fitting these points on two sinewaves, the inspired sinewave 42 and expired sinewave 43 are obtained. These sinewaves are the basis to determine cardiopulmonary parameters in an inspired sinewave test.

Description of the Apparatus and Method to Mix Concentrations

At the core of the inspired sinewave technique, the inspired concentrations of the indicator gases need to follow sinewave patterns, which are defined by the following equations:

For $O_2$:

$$F_{O_2}(t) = \Delta F_{O_2} \times \sin\left(\frac{2\pi}{T_{O_2}}t + \varphi_{O_2}\right) + \overline{F}_{O_2} \quad (1)$$

For $N_2O$:

$$F_{N_2O}(t) = \Delta F_{N_2O} \times \sin\left(\frac{2\pi}{T_{N_2O}}t + \varphi_{N_2O}\right) + \overline{F}_{N_2O} \quad (2)$$

in which $\Delta F_{O_2}$ and $\Delta F_{N_2O}$ are the magnitudes, $T_{O_2}$ and $T_{N_2O}$ are the periods, $\varphi_{O_2}$ and $\varphi_{N_2O}$ are the phase shifts, and $\overline{F}_{O_2}$ and $\overline{F}_{N_2O}$ are the means of $O_2$ and $N_2O$ sinewaves respectively.

During the inspired sinewave test, the desired inspired concentrations of an n-th breath are then determined as the values of sinewaves (1), (2) at the starting time of the n-th inspiration:

$$F_{O_2,desired,n} = F_{O_2}(t_{insp,n}^{start}) \quad (3)$$

$$F_{N_2O,desired,n} = F_{N_2O}(t_{insp,n}^{start}) \quad (4)$$

The desired concentrations of the inspired gases are then obtained by the gas mixing apparatus described earlier (16, 17, 18, 19 of FIG. 1) and an algorithm to set the desired $N_2O$ and $O_2$ as follows.

Consider the conservation of mass for the breathing tube 11:

For all gases $$\dot{V}_{intake} + \dot{V}_{O2} + \dot{V}_{N2O} = \dot{V}_{inspired} \quad (5)$$

where $\dot{V}_{intake}$ is the rate of total volume of gases taken-in by the tube 11, which can come from air (for spontaneous breathing) or ventilators (for ventilated patients); $\dot{V}_{O2}$ is rate of $O_2$ injected to the tube 11; $\dot{V}_{N2O}$ is the rate of $N_2O$ injected to the tube 11; $\dot{V}_{inspired}$ is the rate of gases inspired by the subject.

For $O_2$:

$$F_{O2,intake} \times \dot{V}_{intake} + 100\% \times \dot{V}_{O2} = F_{O2,desired} \times \dot{V}_{inspired} \quad (6)$$

where $F_{O2,intake}$ and $F_{O2,desired}$ are the $O_2$ concentrations of the intake and inspired gases respectively.

For $N_2O$:

$$F_{N2O,intake} \times \dot{V}_{intake} + 100\% \times \dot{V}_{N2O} = F_{N2O,desired} \times \dot{V}_{inspired} \quad (7)$$

where $F_{N2O,intake}$ and $F_{N2O,desired}$ are the $N_2O$ concentrations of the intake and inspired gases respectively.

With $\dot{V}_{inspired}$ measured by the flow sensor 13 in real time (and provided via the feedback control loop indicated in FIG. 1), and $F_{O2,intake}$ and $F_{N2O,intake}$ known, the required $\dot{V}_{O2}$ and $\dot{V}_{N2O}$ to be injected into the breathing tube 11 can be determined by solving equations (5), (6) and (7).

The invention is not limited to only two gases, $O_2$ and $N_2O$. More gases (such as argon) can be easily added and the same principle can be applied to obtain the desired concentrations. Moreover, for flexibility, an additional gas port can also be installed on the breathing tube to release some gases. This flexibility is useful when connecting the device to ventilators and an exact tidal volume is desirable.

The method described by equations (5), (6), (7) does not consider the dynamics of mass flow controllers, hardware limitations, and time delay. Even with the best effort, the desired concentrations cannot be obtained with absolutely no error. A possible solution is to incorporate an additional feedback control loop (in addition to the internal control loops of the mass flow controllers and the flow feedback loop). However, this could be costly and may not eliminate error entirely. A more flexible approach is to consider and compensate for the error in the estimations of cardiopulmonary parameters. Such a compensation algorithm for the estimation of dead space is described in the following section.

Estimation of Dead Space ($V_D$)

Airway dead space is an important parameter regarding the efficiency of ventilation and its relation to pulmonary perfusion (Tang et al., 2006), with applications in respiratory physiology, clinical anaesthesia, and critical care medicine. In the present embodiments, a method to estimate dead space, based on the Bohr method and taking into account the non-uniform inspired concentration caused by noise and error in mixing gases method, is described as follows.

The Bohr method assumes that the inspired concentration of the indicator gas is uniform and constant so that $$F_I(t) = F_{IA}(t) = F_I \quad (8)$$

in which $F_I(t)$ is the inspired concentration of a tracer gas, and $F_{IA}(t)$ is the inspired concentration of the same tracer gas "seen" by the alveoli. From the mass balance equation, the general Bohr equation can be derived as:

$$V_D = V_T \frac{F_A - F_E}{F_A - F_I} \quad (9)$$

in which $V_D$ is the dead space, $V_T$ is the tidal volume, and $F_I$, $F_A$ and $F_E$ are the inspired, alveolar, and mixed expired concentrations respectively. For the special case of $CO_2$, there is no $CO_2$ in the dead space at the end of an inspiration, i.e. $F_{I,CO2} = 0$. The Bohr dead space becomes (Tang et al., 2006; West, 2008):

$$V_{D,CO2} = V_T \frac{F_{A,CO2} - F_{E,CO2}}{F_{A,CO2}} \quad (10)$$

When the concentration of the inspired indicator gas is non-uniform, such as shown in FIG. 3, the dead space estimation method such as Bohr equations (9, 10), or U.S. Pat. No. 6,599,252 B2 (Starr, 2003) cannot be applied. In embodiments of the present invention, we propose a modified Bohr method as follows.

Figure 5:
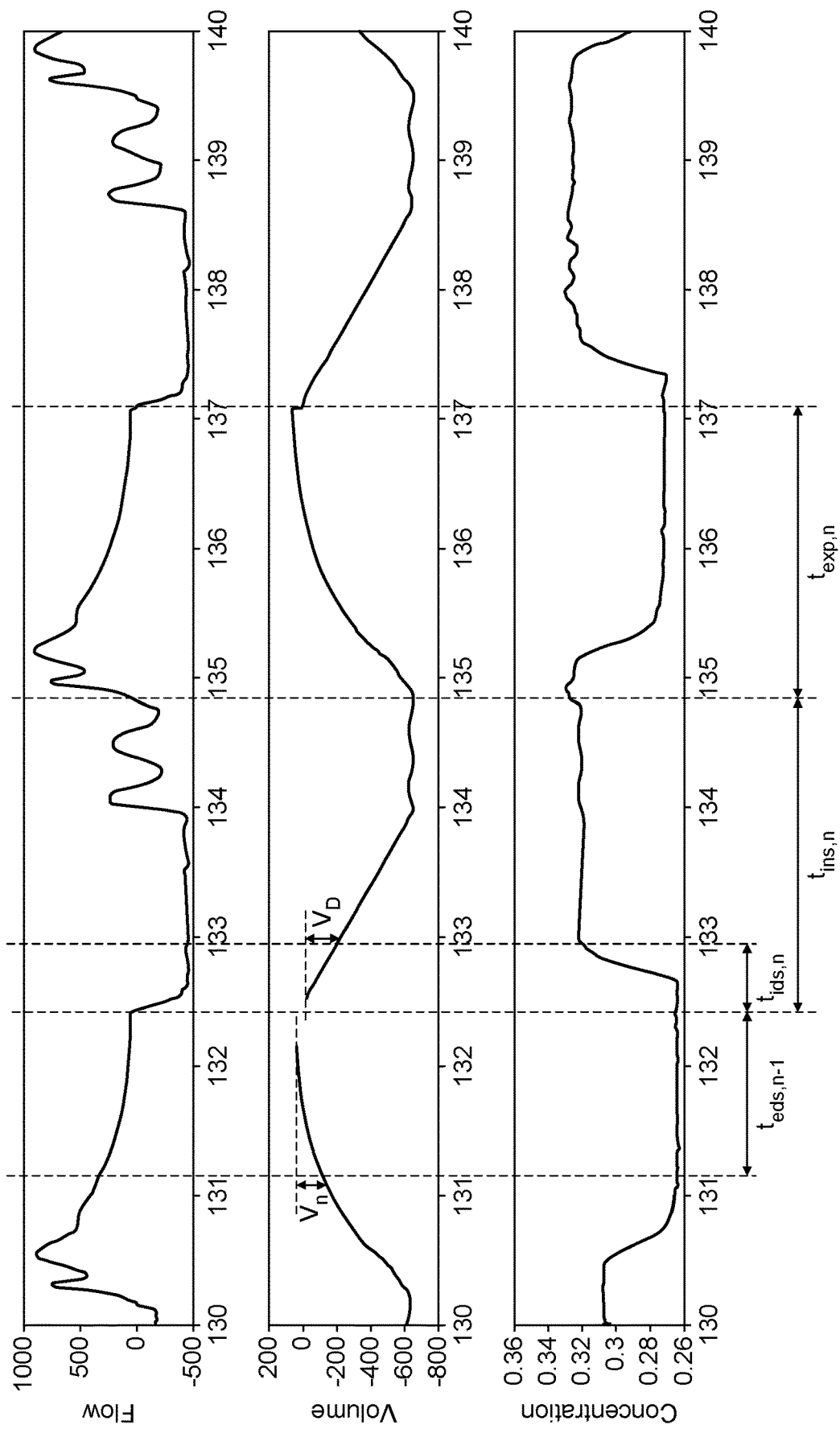
FIG. 5 shows an example of the breathing patterns during an inspired sinewave test, and how the portions of gases remaining in the dead space are determined, also accounting for variations in the inspired concentrations, according to an embodiment of the invention.
Figure 6:
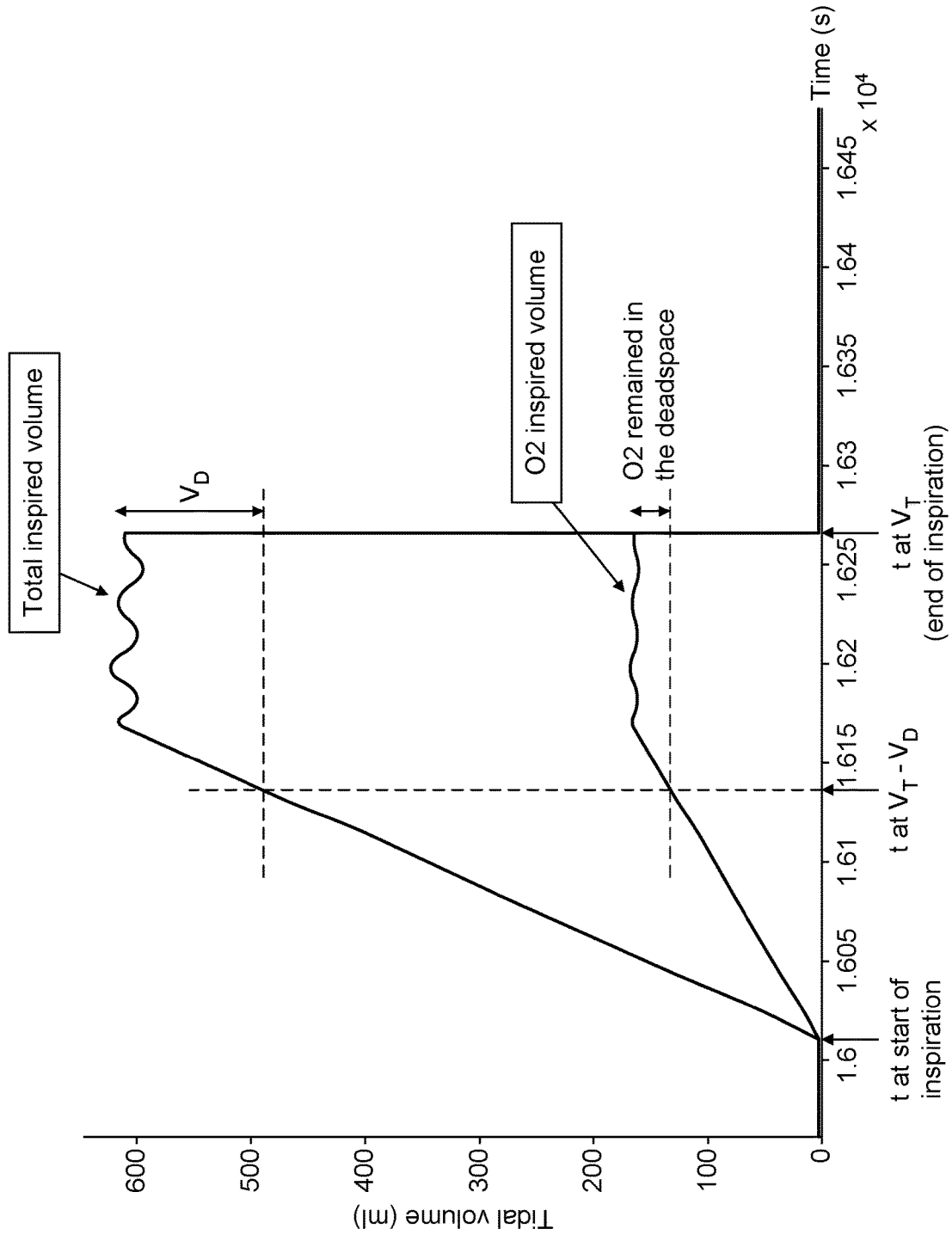
FIG. 6 shows how the dead space may be computed from tidal volume and the volume of the indicator gas remaining in the dead space according to equation (15), details of which are described below in relation to an embodiment of the invention.

The gases that pass the lips consist of two parts. One part travels down to the alveoli level and is "seen" by the alveolar compartment. The other part never reaches the alveolar compartment and remains in the dead space. FIG. 5 demonstrates how the two parts are defined during inspirations and expirations. In FIG. 5, $t_{ins,n}$ and $t_{exp,n}$ are the inspiration and expiration times respectively of a breath circle. For two subsequent breaths, the part of expired gas that remains in the dead space at the end of expiration will be re-inhaled by the next inspiration, and is defined as $t_{eds,n-1}$ and $t_{ids,n}$ for inspiration and expiration respectively. The total inspired volume and inspired indicator volume that pass the lips during an inspiration are then calculated respectively from the flow and concentration signals as:

$$\text{total inspired gas volume} = \int_{t_{insp}}^{t} \dot{V}_T(t) \times dt \tag{11}$$

and $$\text{inspired indicator gas volume} = \int_{t_{insp}}^{t} F_I(t) \times \dot{V}_T(t) \times dt \tag{12}$$

where $t_{insp}$ is the time at the start of inspiration, and $\dot{V}_T(t)$ is the inspired flow rate. An example of these two functions is demonstrated in FIG. 6.

The indicator gas remaining in the dead space at the end of an n-th inspiration is:

$$\text{indicator gas remained in the dead space}_{n-th} = \int_{t_{VT-VD}}^{t_{VT}} F_I(t) \times \dot{V}_T(t) \times dt \tag{13}$$

where $t_{VT-VD}$ is the time after which any gas that passes the lips only fills the dead space, and $t_{VT}$ is the time at the end of the inspiration. With $V_D$ unknown, equation (13) can be interpreted as a function of dead space where $V_D$ can take a value between 0 and $V_T$:

$$f(V_D) = \int_{t_{VT-VD}}^{t_{VT}} F_I(t) \times \dot{V}_T(t) \times dt \tag{14}$$

As the indicator gas remaining in the dead space at the end of an inspiration will go out in the next expiration, the mass balance equation becomes:

$$\text{indicator gas}_{out} = \text{indicator gas}_{deadspace} + F_A \times (V_T - V_D)$$

$$\Leftrightarrow F_E \times V_T = f(V_D) + F_A \times (V_T - V_D)$$

$$\Leftrightarrow f(V_D) - F_A \times V_D = (F_E - F_A) \times V_T \tag{15}$$

Figure 7:
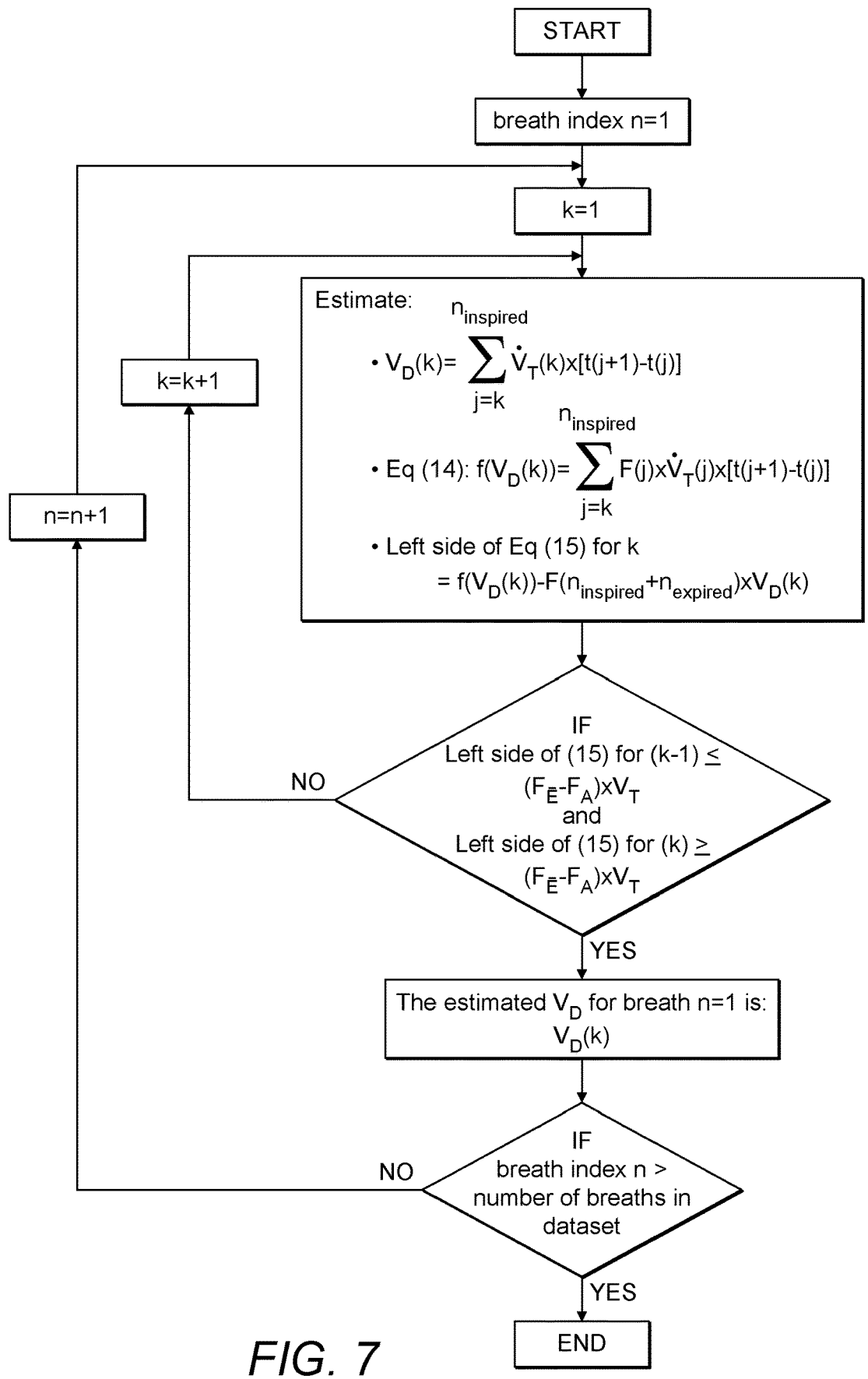
FIG. 7 details a computational algorithm that is used in an embodiment of the invention to solve equation (15)

By solving equation (15), the dead space can be calculated for each breath. FIG. 7 details the computational algorithm that is used in embodiments of the invention to solve equation (15).

Once the dead space values for all the breaths are determined, a robust estimation method such as an M-estimator proposed by (Huber and Ronchetti, 2009) is used to determine the final dead space value and the 95% confidence interval:

$$\hat{V}_{D,final} = \underset{\theta}{\operatorname{argmin}} \left( \sum_{n=1}^{n\_total} \rho(V_{D,n}, \theta) \right) \tag{16}$$

in which $\theta$ is the parameter to estimate final dead space value, $V_{D,n}$ is the dead space value estimated for the n-th breath, and $\rho(V_{D,n},\theta)$ is the Huber loss function:

$$\rho(V_{D,n}, \theta) = \begin{cases} \frac{1}{2}(V_{D,n} - \theta)^2 & \text{for } |V_{D,n} - \theta| < k \\ k|V_{D,n} - \theta| - \frac{1}{2}k^2 & \text{for } |V_{D,n} - \theta| \geq k \end{cases} \tag{17}$$

and k is a constant chosen based on the quality of the data. It should be noted that the invention is not limited to this particular M-estimator; more sophisticated robust methods can also be used to remove outliers and improve the estimation of the final value of dead space.

Figure 8:
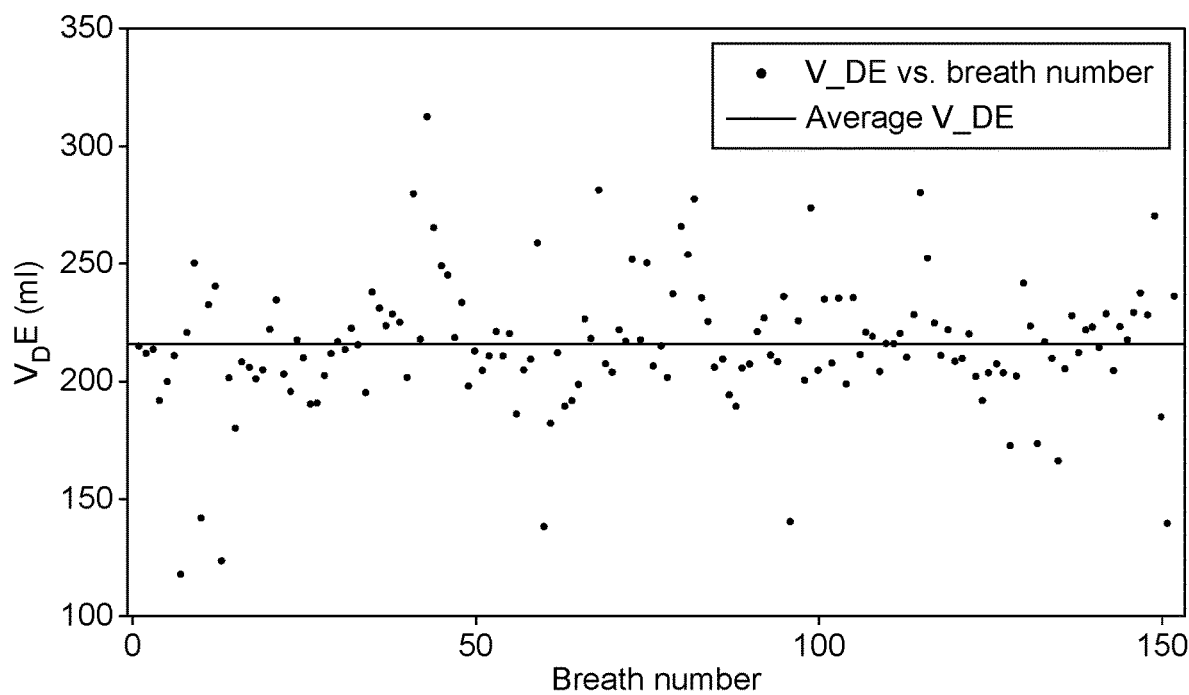
FIG. 8 shows an example of dead space estimation for an inspired sinewave test, with the dots representing values of dead space estimated in individual breaths, and the horizontal line representing the mean dead space, obtained after outliers are removed.

FIG. 8 demonstrates an example of how the dead space is determined over 150 breaths by the device after removing outliers. The dots represent values of dead space estimated in individual breaths. The horizontal line is the mean dead space, obtained after outliers are removed.

Table 1 below sets out the results of a comparison study between the previous method (of Clifton et al., 2013 (two references)) and the present new method to estimate lung dead space, in three different setups of a laboratory mechanical bench lung with known dead space. This shows that the present new method produces much smaller error and standard deviation values compared to the previous method.

TABLE 1

The results of a comparison study between the previous method (of Clifton et al., 2013 (two references)) and the present new method to estimate lung dead space, in three different setups of a laboratory mechanical bench lung with known dead space.

| | | | |
|---|---|---|---|
| Actual dead space set on the mechanical bench lung | 118 ml | 208 ml | 258 ml |
| Dead space estimated by previous method | 228 ± 26 ml | 327 ± 20 ml | 393 ± 26 ml |
| Dead space estimated by new method | 110 ± 10 ml | 206 ± 8 ml | 260 ± 8 ml |
| Error of previous method | 110 ± 26 ml | 119 ± 20 ml | 135 ± 26 ml |
| Error of new method | 8 ± 10 ml | −2 ± 8 ml | 2 ± 8 ml |

Figure 9:
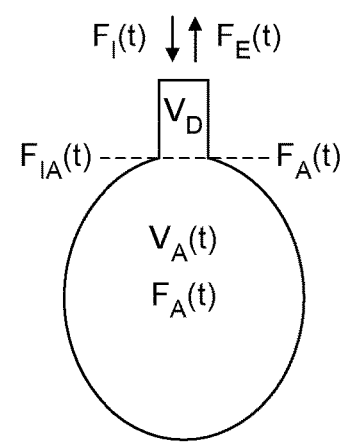
FIG. 9 shows a tidally ventilated "balloon on a straw" model of the lung.

Estimating Functional Residual Capacity (FRC) and Pulmonary Blood Flow $\dot{Q}_P$ Embodiments of the invention also provide a method to determine the functional residual capacity and pulmonary blood flow simultaneously and breath by breath. These two cardiopulmonary parameters are determined based on the tidal "balloon on a straw" lung model (Hahn and Farmery, 2003) shown in FIG. 9. The lung is considered as a single serial dead space connected to a single compartment lung. $F_I(t)$ is the inspired concentration as a function of time t. $F_{IA}(t)$ is the inspired concentration "seen" by the alveolar at time t. $V_A(t)$ and $F_A(t)$ are the volume and tracer concentration in the alveolae respectively, and $F_E(t)$ is the expired concentration.

The dead space is defined as the portion of inspired gas that passes the lips but never gets to the alveolar compartment. During respiration, the lung extends from end-tidal volume $V_A$ to $V_A + V_T$ in which $V_T$ is the tidal volume. Taking into account the non-uniform variation of the inspired concentrations, the mixed inspired concentration of a tracer gas "seen" by the alveoli is calculated by:

$$F_{IA,n} = \frac{1}{V_{T,n} - V_D} \int_{t_{0,n}}^{t_{VT,n}-VD} F_I(t) \times f(t) \, dt \tag{18}$$

in which $t_{0,n}$ is the time at the start of inspiration of the n-th breath, $t_{VT,n-VD}$ is the time after which any gas that passes the lips only fills the dead space of the n-th breath.

From the conservation of mass and some mathematical manipulation, the equation governing the relationship of $V_A$ and $\dot{Q}_P$ is:

$$V_A \times (F_{A,n} - F_{A,n-1}) + \lambda \times \dot{Q}_P \times (F_{A,n} - F_v) \times \Delta t_n = V_D \times (F_{IA,n} - F_{A,n-1}) + V_{T,n} \times (F_{A,n} - F_{IA,n}) \tag{19}$$

in which $V_A$ is the alveolar volume, $V_D$ is the dead space volume estimated by the aforementioned method, $V_{T,n}$ is the tidal volume of the n-th breath, $\lambda$ is the solubility of a tracer gas (0.47 for $N_2O$ for example), $\dot{Q}_P$ is the pulmonary blood flow, $\Delta t_n$ is the respiration of the n-th breath, $F_{A,n}$ is the alveolar concentration of the n-th breath, $F_V$ is the concentration of the mixed venous sinewave, and $F_{\overline{I},n}$ is the mixed inspired concentration of an indicator gas as 'seen' by the alveolar compartment.

At reasonable short periods (e.g. less than 5 minutes), the concentration sinewave in the mixed venous blood is so diminished that it can be assumed a constant, equal to the mean. The periods of the applied inspired sinewaves are carefully chosen such that this condition is satisfied. Equation (19) becomes:

$$V_A \times (F_{A,n}-F_{A,n-1}) + \lambda \times \dot{Q}_P \times (F_{A,n}-\overline{F}_A) \times \Delta t_n = V_D \times (F_{\overline{I},n}-F_{A,n-1}) + V_{T,n} \times (F_{A,n}-F_{\overline{I},n}) \quad (20)$$

in which $\overline{F}_A$ is the concentration of the mixed venous sinewave.

Figure 10:
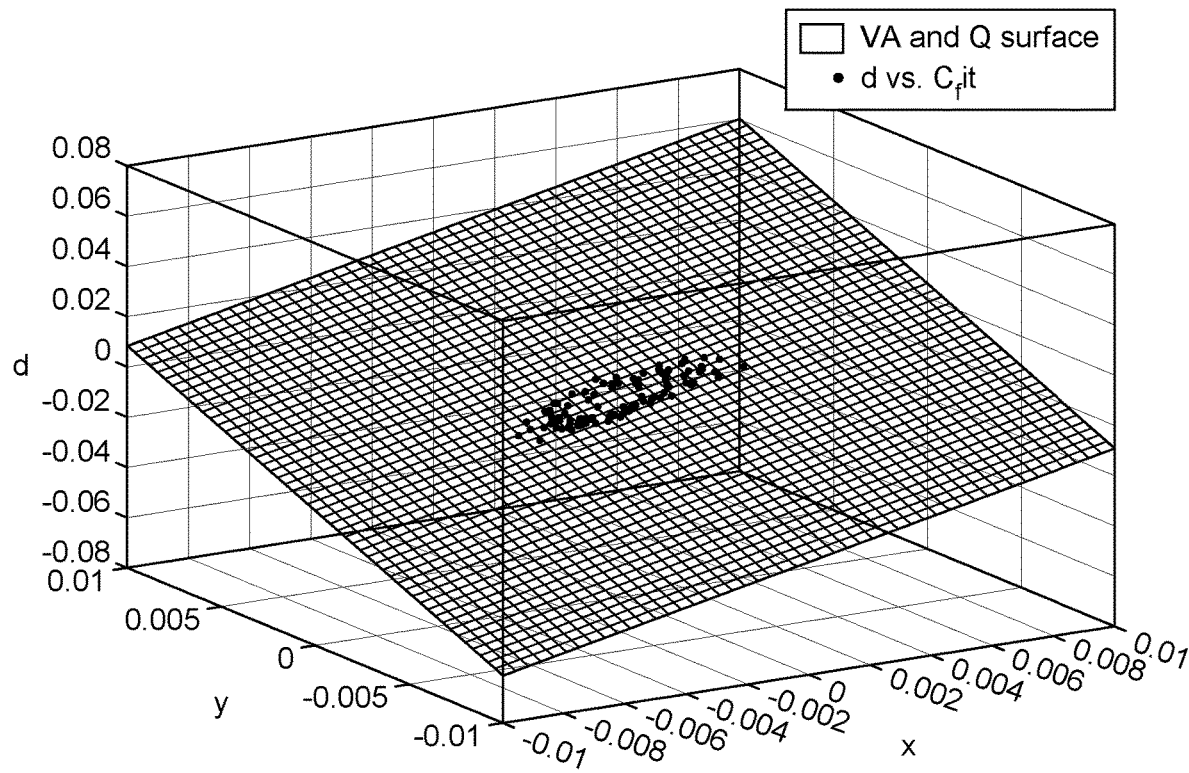
FIG. 10 demonstrates the determination of FRC and pulmonary blood flow as the slopes of a 3D surface.

As $F_{A,n}$, $F_{A,n-1}$, $\Delta t_n$, $F_{I,n}$, $V_{T,n}$ can be measured or estimated from the sensors, for each breath n, a point $P_n(x_n, y_n, z_n)$ in 3-dimension (x,y,z) can be computed using equation (20):

$$x_n = F_{A,n} - F_{A,n-1}$$

$$y_n = \lambda \times (F_{A,n} - \overline{F}_A) \times \Delta t_n$$

$$z_n = V_D \times (F_{I,n} - F_{A,n-1}) + V_{T,n} \times (F_{A,n} - F_{I,n}) \quad (21)$$

and a 3D surface $V_A \times x + \dot{Q}_P \times y = z$ can be constructed from the points, in which $V_A$ and $\dot{Q}_P$ are the slopes of the constructed surface. Alternative to the standard least square estimation method, maximum likelihood estimation techniques such as bisquare can be used to remove outliers to give the robust estimations of $V_A$ and $\dot{Q}_P$ and their corresponding 95% confidence intervals. FIG. 10 demonstrates how alveolar volume and pulmonary blood flow can be estimated using equations (20, 21) in an inspired sinewave test.

Having determined $V_A$ in this way, FRC can then be estimated through the relationship $FRC = V_D + V_A$ with $V_D$ being determined as discussed above.

Figure 11:
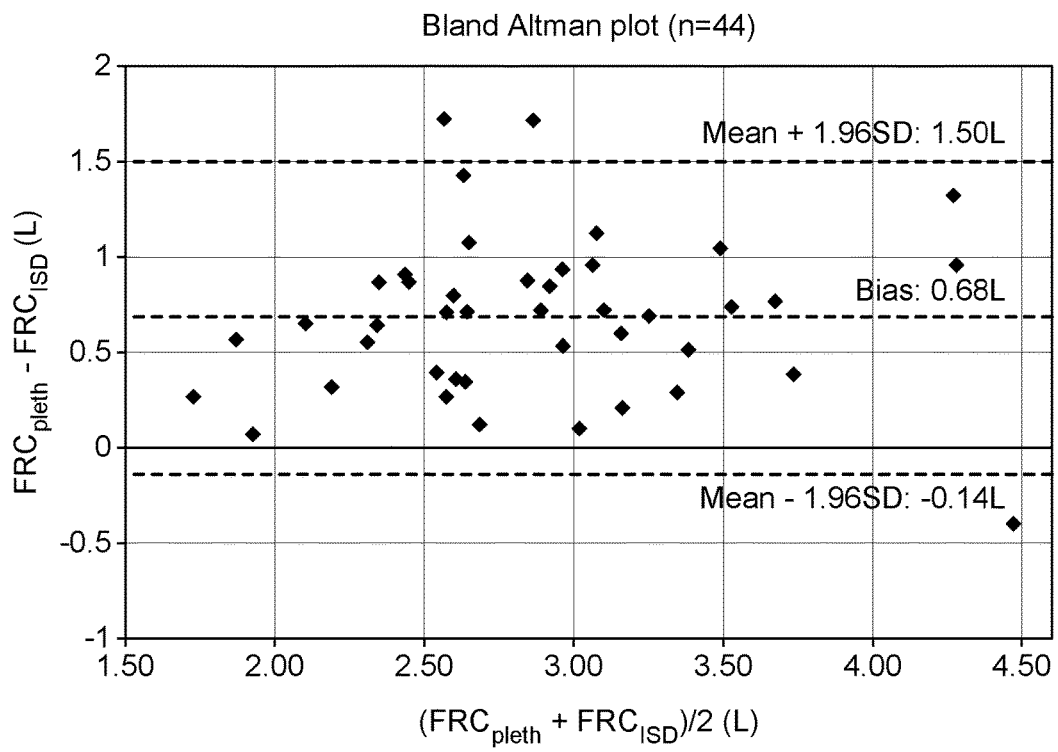
FIG. 11 shows a Bland Altman Plot comparing FRC measurements by Body Plethysmography and FRC estimations by an Inspired Sinewave Device according to an embodiment of the present invention.

FIG. 11 demonstrates the estimation of FRC by the methods described in this work in comparison to the gold standard body plethysmography, showing a good agreement between two methods and a bias of 0.6 L. The bias of 0.6 L is comparable to other respired gases techniques when comparing with the body plethysmography. Past and ongoing clinical research suggests that body plethysmography often overestimates FRC in comparative studies involving chest Computed Tomography (CT) and Helium Dilution. Possible reasons include presence of gas in abdominal cavities and a degree of dependency of panting frequency on mouth—alveoli pressure equilibration. Helium Dilution often underestimates lung volume due to effects of gas trapping, although both anomalies are thought to be less pronounced in healthy subjects.

Figure 12:
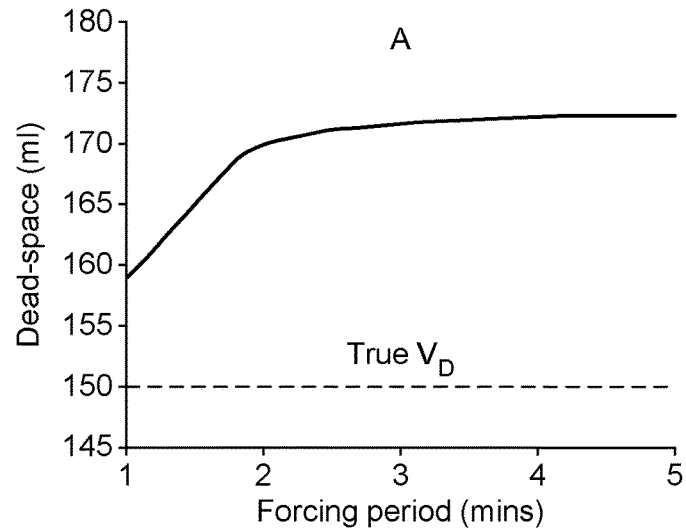
FIG. 12 shows a simulation study of frequency/period response of an inhomogeneous lung, with the solid lines showing the effective lung parameters as functions of forcing periods, and the dashed lines showing the values that would be the lung parameters if the lung was perfectly homogeneous.
Figure 12:
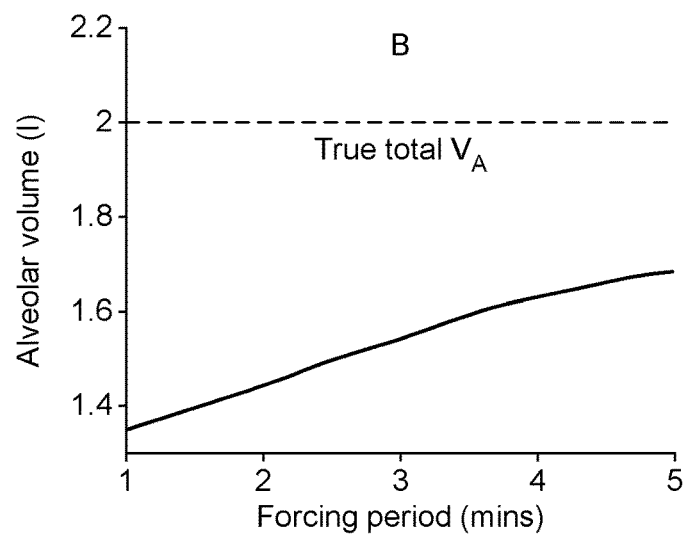
Figure 12:
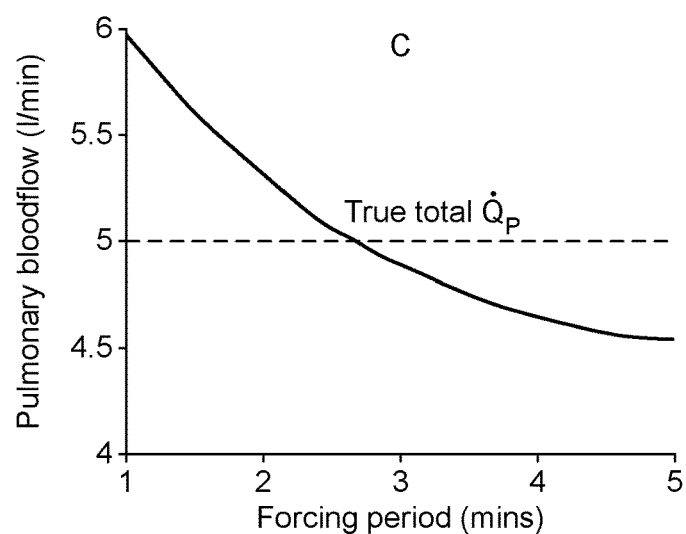

Due to lung inhomogeneity as shown in FIG. 12 and FIG. 13, $V_A$ estimated at shorter sinewave periods underestimates actual volume. On the other hand, $\dot{Q}_P$ estimated at longer sinewave periods becomes unreliable due to the fact that, at longer periods, the sinusoidal signal in the recirculating venous blood becomes sizeable and cannot now be neglected. The sinewave period of 3 minutes is chosen clinically to provide the most accurate and reliable estimations:

$$FRC = V_D + V_A(3 \text{ mins}) \quad (22)$$

$$\dot{Q}_P = \dot{Q}_P(3 \text{ mins}) \quad (23)$$

in which FRC is the functional residual capacity, $V_A$(3 mins) and $\dot{Q}_P$(3 mins) are the alveolar volume and pulmonary blood follow estimated using a sinewave period of 3 mins.

Measurement of Inhomogeneity

The clinical value measuring lung inhomgeneity is that traditional tests of lung function (peak flow, forced vital capacity in 1 second, forced expiratory volume (FEV1), etc.) are notoriously insensitive. Significant abnormalities in FEV1 are only evident when the diagnosis is well established and disease moderately advanced and severe. It is established that ventilatory and V/Q inhomogeneity become abnormal in the early, subclinical stages of many respiratory diseases such as chronic obstructive pulmonary disease (COPD) and cystic fibrosis. These changes are detectable on hyperpolarized Xenon MRI scanning, but there is currently no clinically reliable test for these subtle changes which can be simply deployed in the clinic or at the bedside.

A key advantage of using inspired sinewaves is the dependency of the recovered parameters on the chosen sinewave periods. This dependency provides insight and useful information about, and quantification of the degree inhomogeneity of ventilation and ventilation:perfusion ratio throughout the lung. However, no method has been described in the state of the art to process the frequency/period dependency of the recovered parameters, or to use this to provide a quantification of lung inhomogeneity. It is the purpose of an embodiment of the present invention to provide such a method, with details given as follows.

FIG. 12 shows a simulation study with a tidal inhomogeneous lung model, demonstrating that lung parameters recovered depends on the periods of the sinewaves applied, and that level of dependency reflects lung inhomogeneity.

Figure 13A:
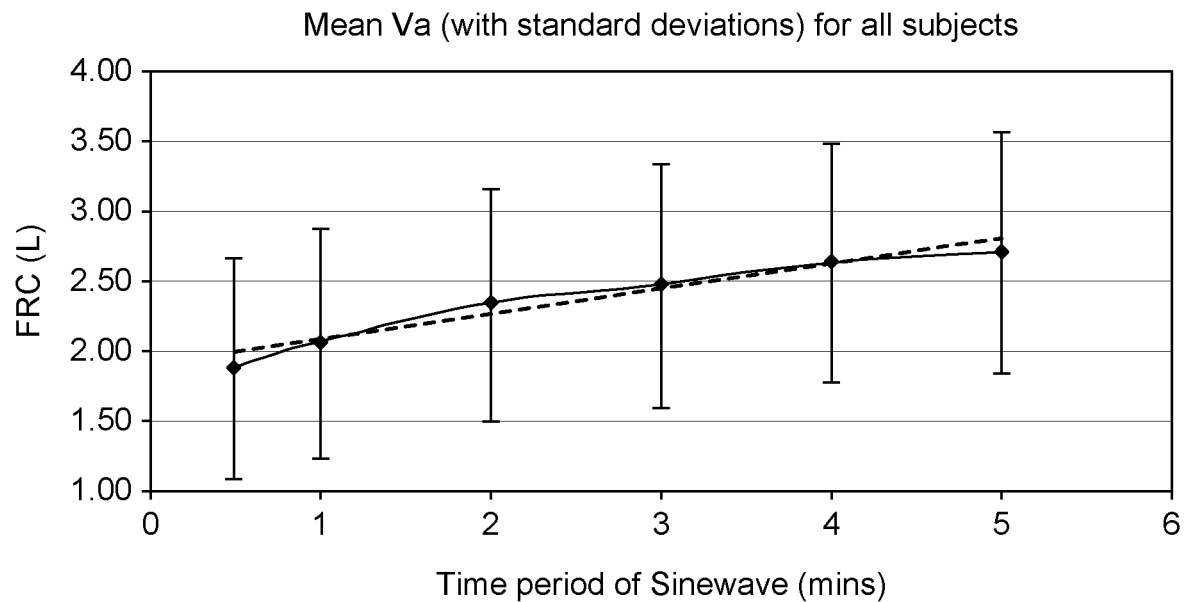
FIG. 13a shows the period dependency of recovered FRC in a group of healthy volunteers.
Figure 13B:
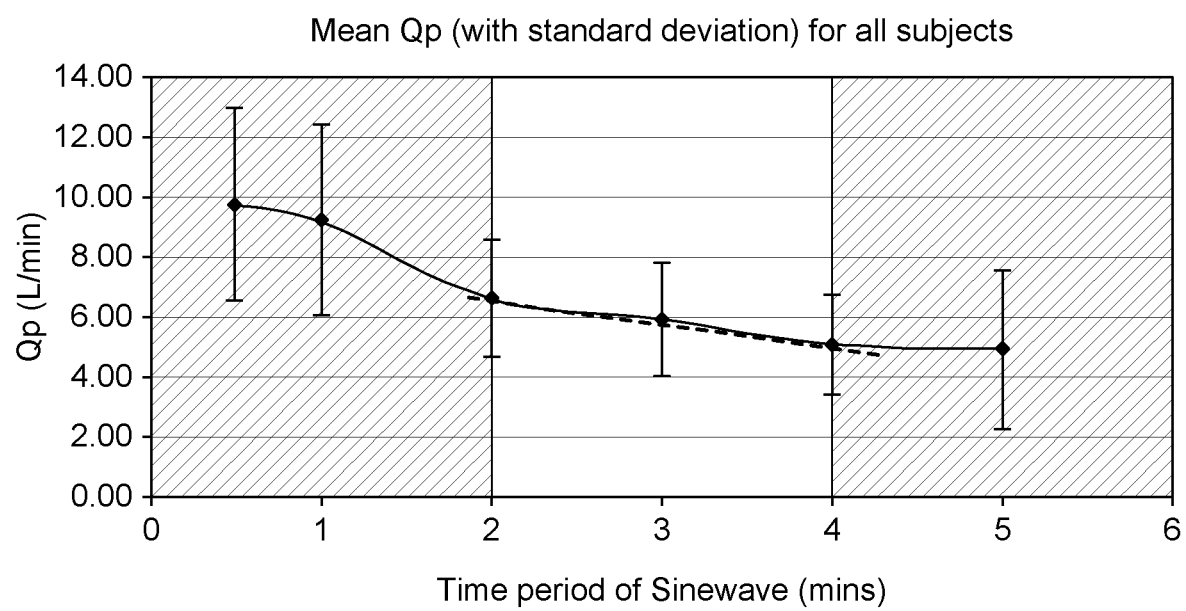
FIG. 13b shows the corresponding period dependency of pulmonary blood flow ($\dot{Q}_P$), obtained using an embodiment of the present invention.

FIGS. 13a and 13b display the mean response of a group of healthy subjects obtained by the methods of the present work, as described above, across a range of sinewave periods. FIG. 13a shows the sinewave period dependency of recovered FRC, and FIG. 13b shows the corresponding period dependency of pulmonary blood flow $\dot{Q}_P$ (although identified simply as "$Q_P$" in the graph). With reference to FIG. 13b, for robust and accurate estimation the method only uses values between 2 mins and 4 mins for estimation of pulmonary blood flow. Pulmonary blood flows below 2 mins and above 4 mins are affected by noise sensitivity and recirculation. Details of the steps used to obtain these data are described above.

Index of ventilation-volume inhomogeneity is represented by the gradient (dashed line) of the period response on the FRC graph in FIG. 13a. Similarly, index of ventilation-perfusion inhomogeneity is represented by the gradient of the period response between 2 mins and 4 mins, on the $\dot{Q}_P$ graph in FIG. 13b.

There is a small degree of inhomogeneity even in healthy subjects compared to the ideal lung, and the slopes of the response reflect the degree of inhomogeneity. For sinewave periods smaller than 2 mins, the pulmonary blood flow estimated is sensitive to noise, whereas for sinewave periods larger than 4 mins, the pulmonary blood flow estimated is inaccurate due to excessive recirculation of the venous signal. The period range of interest for pulmonary blood flow is therefore between 2 mins and 4 mins.

Figure 14:
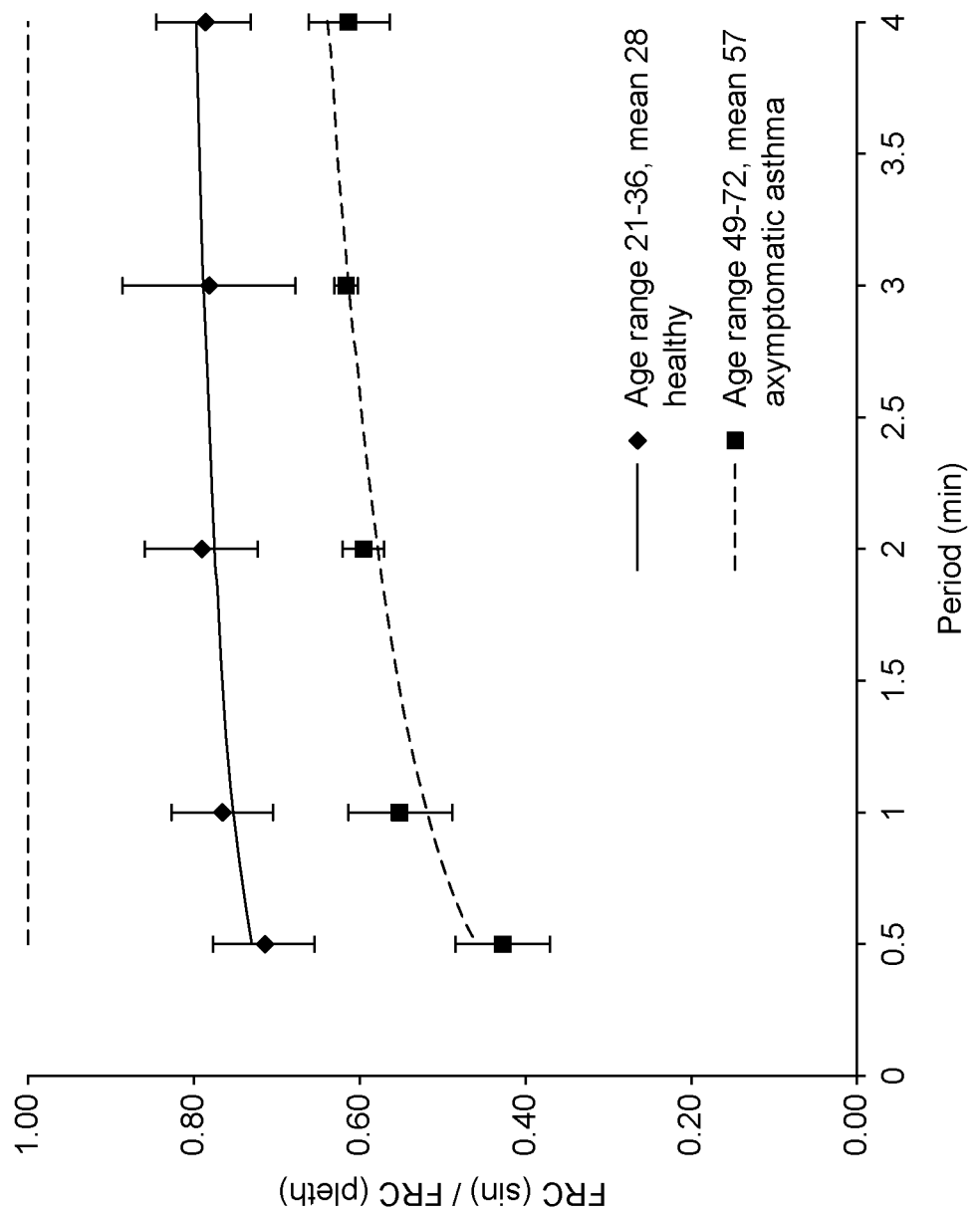
FIG. 14 shows the inhomogeneity difference in groups of healthy young subjects (solid line), and asymptomatic asthma subjects (dashed line)

During an inspired sinewave test, a subject is tested at different sinewave periods such as 0.5, 1, 2, 3, 4, 5 mins. The results can then be used to construct a period response of the subject. This period response is then plotted against normalised maps of healthy and diseased groups such as the ones shown in FIG. 14, to derive a measurement of inhomogeneity. In addition, to quantify the inhomogeneity, embodiments of the present invention also define four indices as:

$$I_1 = \frac{V_A(4 \text{ mins}) - V_A(0.5 \text{ mins})}{V_A(0.5 \text{ mins})} \quad (24)$$

$$I_2 = \frac{V_{A,predict}}{V_A(0.5 \text{ mins})} \quad (25)$$

$$I_3 = \frac{V_{A,plethysmograph}}{V_A(0.5 \text{ mins})} \quad (26)$$

$$I_4 = \frac{\dot{Q}_P(2 \text{ mins}) - \dot{Q}_P(4 \text{ mins})}{\dot{Q}_P(4 \text{ mins})} \quad (27)$$

in which $V_A(0.5 \text{ mins})$, $V_A(4 \text{ mins})$ are the lung volume estimated at sinewave periods of 0.5 minutes and 4 minutes respectively; $\dot{Q}_P(2 \text{ mins})$, $\dot{Q}_P(4 \text{ mins})$ are the pulmonary blood flow estimated at sinewave periods of 2 minutes and 4 minutes respectively, $V_{A,plethysmograph}$ is the lung volume measured by body plethysmography if available, and $V_{A,predict}$ is the predicted lung volume calculated from the height and weight of the subject, for example by the formula (Quanjer et al., 1993):

$$V_{A,predict} = \begin{bmatrix} 2.34 \times \text{height} + 0.01 \times \text{age} - 1.09 - V_D, & \text{male} \\ 2.24 \times \text{height} + 0.01 \times \text{age} - 1 - V_D, & \text{female} \end{bmatrix} \quad (28)$$

$I_1$, $I_2$, $I_3$ reflect inhomogeneity in only ventilation-volume, whereas $I_4$ reflects the inhomogeneity in both ventilation-volume and ventilation-perfusion. The larger these indices, the higher the level of inhomogeneity, and so these have diagnostic significance. For example, FIG. 14 demonstrates the inhomogeneity difference in groups of healthy young and asymptomatic asthma. For a healthy young group, $I_1=0.09$ and $I_3=1.43$. For an asymptomatic asthma group, $I_1=0.38$ and $I_3=2.38$.

Figure 15:
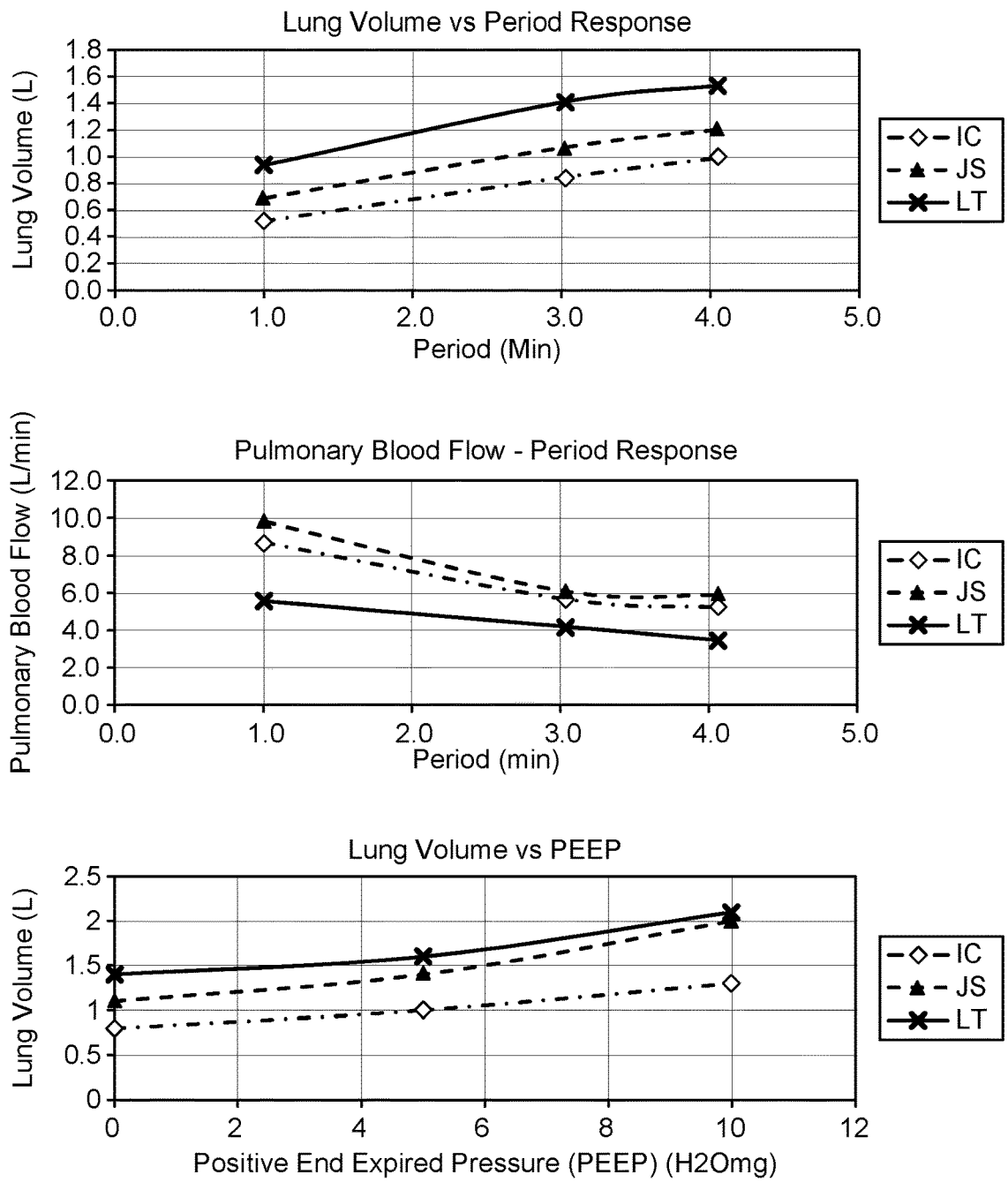
FIG. 15 shows inspired sinewave test results of three adult ventilated patients in operating theatres, obtained using an embodiment of the present invention, showing the period response of lung volume and pulmonary blood flow and also the change of lung volume versus positive end expired pressure setting (with details of the three patients being given in the table at the bottom of the figure).

FIG. 15 demonstrates the use of an embodiment of the present invention in three adult ventilated patients in operating theatres. It shows the period response of lung volume and pulmonary blood flow and also the change of lung volume versus positive end expired pressure setting. Details of the three patients used in these trials are given in the table at the bottom of FIG. 15.

Summary

The present work provides inter alia the following:
1) Apparatus to mix inspired gas at the mouth of patients, comprising:
   one or more mass flow controllers;
   an accurate real-time flow sensor;
   a diffusing injector in the breathing tube; and
   computer software and algorithm to control the mixing of the gases according to the breathing flow of the patients.
2) Apparatus to determine total amounts of inspired/expired gas at the mouth of the patient, comprising:
   an accurate real-time flow sensor;
   a mainstream fast-response gas analyser; and
   computer software and algorithm to line up signals, compensate and integrate to determine the correct amount of gases.
3) A computer control interface of the inspired sinewave device, which includes:
   displays of flow and concentrations of gases in real time;
   control panels allowing real time adjustment of magnitudes, phases, means, and periods of the sinewaves of the indicator gases delivered to the patients; and
   displays of inspired sinewave test results, calculated inspired and expired sinewaves, and table of estimated dead space ±95% confidence interval, estimated FRC ±95% confidence interval, pulmonary blood flow ±95% confidence interval
4) A method to robustly estimate dead space breath by breath for non-uniform indicator gases.
5) A method to estimate functional residual capacity and pulmonary blood flow simultaneously, breath by breath.
6) A method to investigate lung inhomogeneity from the inspired sinewave tests at different periods, including (but not limited to) four indices.

REFERENCES

Choncholas, G. J., Gosenheimer, B. M., Micheli, P. R., 2007. Ventilator. EP1767235 A2.

Clemensen, P. C., Nielsen, J. G., 2009. Method to compensate for the effect of recirculation of inert blood soluble gas on the determination of pulmonary blood flow in repeated inert gas rebreathing tests. US20090320844 A1.

Clemensen, P. C., Nielsen, J. G., 2011. Combination of inert gast rebreathing and multiple-breath wash-out techniques for determination of indices of ventilation inhomogeneity. EP2311371 A1.

Clifton, L., Clifton, D. A., Hahn, C. E. W., Farmery, A. D., 2013. Assessment of lung function using a non-invasive oscillating gas-forcing technique. Respir. Physiol. Neurobiol. 189, 174-182.

Clifton, L., Clifton, D. A., Hahn, C. E. W., Farmery, A. D., 2013. A Non-Invasive Method for Estimating Cardiopulmonary Variables Using Breath-by-Breath Injection of Two Tracer Gases. IEEE Journal of Translational Engineering in Health and Medicine 1, 1-8.

Hahn, C. E. W., Farmery, A. D., 2003. Gas exchange modelling: no more gills, please. Br. J. Anaesth. 91, 2-15.

Huber, P. J., Ronchetti, E., 2009. Robust statistics. Wiley, Hoboken, N.J.

Larsson, A., Castor, R., Brauer, S., Olsson, S., 1999. Method by determination of the functional residual capacity of lungs and a ventilator device for the determination of the functional residual capacity. EP0653183.

Quanjer, P. H., Tammeling, G. J., Cotes, J. E., Pedersen, O. F., Peslin, R., Yernault, J. C., 1993. Lung volumes and forced ventilatory flows. Report Working Party Standardization of Lung Function Tests, European Community for Steel and Coal. Official Statement of the European Respiratory Society. Eur. Respir. J. Suppl. 16, 5-40.

Starr, E. W., 2003. Method and apparatus for anatomical deadspace measurement. U.S. Pat. No. 6,599,252 B2.

Tang, Y., Turner, M. J., Baker, A. B., 2006. A New Equal Area Method to Calculate and Represent Physiologic, Anatomical, and Alveolar Dead Spaces. Anesthesiology 104.

Weismann, D., Reißmann, H., Maisch, S., Füllekrug, B., Schulte, J., 2006. Monitoring of Functional Residual Capacity by an Oxygen Washin/Washout, Technical Description and Evaluation. J. Clin. Monit. Comput. 20, 251-260.

West, J. B., 2008. Respiratory Physiology: The Essentials. Lippincott Williams & Wilkins.

The invention claimed is:

1. A method for adjusting appropriate ventilator settings in a ventilated patient in need thereof based on information obtained by measuring anatomical dead space $V_D$ in a lung, the method comprising:
   (a) providing, in a supply of inspired gas, at least one indicator gas for inhalation by a patient during use, the concentration of the indicator gas being controlled by a mass flow controller such as to follow a sinewave pattern over successive breaths, wherein the ventilated patient inhales the inspired gas, by a breathing tube, and further wherein the concentration of the indicator gas is controlled, by the mass flow controller, such as to follow a sinewave pattern over successive breaths by:
      (i) providing flow control means for injecting the indicator gas into the supply of inspired gas via the breathing tube;
      (ii) processing, by a processing unit, a measured flow rate and concentration of the inspired indicator gas over each breath so as to determine, by a gas mixing controller, from breath to breath, an injection rate for the inspired indicator gas that will cause the inspired indicator gas to follow said sinewave pattern, and
      (iii) providing feedback control from the gas mixing controller to the flow control means, to cause the flow control means to inject the indicator gas at the determined injection rate, the feedback control based on data comprising the measured flow rate, concentration of the inspired indicator gas, the injection rate from the mass flow controller, the supply of the inspired gas, and feedback from a flow sensor and a gas analyzer each in communication with the breathing tube;
   (b) measuring, by the flow sensor and the gas analyzer, over successive breaths, the flow rate and concentration of the indicator gas during both inspiration and exhalation of the patient;
   (c) fitting sinewave envelopes to the measured concentration values of the indicator gas over the successive breaths and, from the fitted sinewave envelopes, determining, by the system controller, the inspired concentration $F_I$, the mixed expired concentration $F_{\bar{E}}$, and the end expired concentration $F_E$ with respect to the indicator gas for each breath; and
   (d) calculating, by the system controller, the anatomical dead space VD for each of a plurality of inspirations, by:
      (i) calculating the tidal volume $V_T$ for the given inspiration by integrating over time, from the start of that inspiration, the flow rate $\dot{V}_T(t)$ of the inspired gas for that inspiration wherein the tidal volume $V_T$ for each of the plurality of inspirations is calculated using $\int_{t_{insp}} \dot{V}_T(t) \times dt$, where $t_{insp}$ is the time at the start of inspiration and $\dot{V}_T(t)$ is the inspired flow rate;
      (ii) calculating the volume of inspired indicator gas in the given inspiration by integrating over time, from the start to the end of that inspiration, the product of the inspired concentration $F_I$ and the flow rate $\dot{V}_T(t)$ of inspired gas taken from the concentration and flow rate signals respectively, from the start to the end of that inspiration; and
      (iii) calculating the dead space $V_D$ for the given inspiration, based on:
         the tidal volume $V_T$ for that inspiration;
         the inspired concentration $F_I$ of indicator gas taken from the concentration signal, from the start to the end of that inspiration;
         the mixed expired concentration $F_{\bar{E}}$ of indicator gas for that inspiration; and
         the alveolar gas concentration $F_A$ for that inspiration, which is taken as the expired concentration $F_E$ of indicator gas at the end of that expiration;
         the calculating involving a conservation-of-mass principle during expiration, between the amount of indicator gas expired out and the sum of the amount of indicator gas remaining in the dead space and the amount of indicator gas expired from the part of the lung where gas exchange has taken place, whereby, having determined the inspired concentration $F_I$, the flow rate $\dot{V}_T(t)$, the tidal volume $V_T$, the mixed expired concentration $F_{\bar{E}}$, and the alveolar gas concentration $F_A$, a mass balance equation is solved to give an estimation of the dead space $V_D$ for each breath, wherein said mass balance equation comprises $f(V_D)-F_A \times V_D=(F_{\bar{E}}-F_A) \times V_T$;
   (e) varying a period of said sinewave pattern of concentration of the indicator gas over successive breaths during use by the patient;
   determining, at different sinewave pattern periods, values of one or more of the dead space $V_D$, alveolar volume $V_A$, functional residual capacity, and pulmonary blood flow $\dot{Q}_P$;
   providing, by the system controller, a measurement of lung inhomogeneity based on the variation in the determined values with said sinewave pattern period, and
   (f) adjusting ventilator settings in the ventilated patient in need thereof, based on said measurement of lung inhomogeneity, ventilator settings comprising at least one of tidal volume, positive end expiratory pressure, magnitude, phase, means and period of sinewaves of the indicator gases delivered to the patient.

2. The method of claim 1, further comprising applying an estimation method to the calculated anatomical dead space values for the plurality of inspirations, in order to remove outliers and obtain an average dead space value.

3. The method of claim 2, wherein the estimation method provides a 95% confidence interval.

4. The method of claim 3, wherein an M-estimator is used to determine the average dead space value and the 95% confidence interval, the M-estimator using:

$$\hat{V}_{D,final} = \arg\min_{\theta} \left( \sum_{n=1}^{n\_total} \rho(V_{D,n}, \theta) \right)$$

in which θ is the parameter to estimate the dead space value, $V_{D,n}$ is the dead space value estimated for an n-th breath, $\rho(V_{D,n},\theta)$ is a loss function $$\rho(V_{D,n}, \theta) = \begin{cases} \frac{1}{2}(V_{D,n} - \theta)^2 & \text{for } |V_{D,n} - \theta| < k \\ k|V_{D,n} - \theta| - \frac{1}{2}k^2 & \text{for } |V_{D,n} - \theta| \geq k \end{cases},$$

and k is a constant chosen based on the quality of the data.

5. The method of claim 4, further comprising estimating one or both of the alveolar volume $V_A$ and the pulmonary blood flow $\dot{Q}_P$ as slopes of a virtual 3D surface $V_A \times x + \dot{Q}_P \times y = z$, where $$x_n = F_{A,n} - F_{A,n-1}$$

$$y_n = \lambda \times (F_{A,n} - \overline{F}_A) \times \Delta t_n$$

$$z_n = V_D \times (F_{\overline{I},n} - F_{A,n-1}) + V_{T,n} \times (F_{A,n} - F_{\overline{I},n});$$

in which $V_D$ is the dead space volume, $V_{T,n}$ is the tidal volume of an n-th breath, $\lambda$ is the solubility of the indicator gas, $\Delta t_n$ is the respiration time of the n-th breath, $F_{A,n}$ is the alveolar concentration of the n-th breath, $F_v$ is the concentration of the mixed venous sinewave, and $F_{\overline{I},n}$ is the mixed inspired concentration of the indicator gas as 'seen' by the alveolar compartment.

6. The method of claim 5, further comprising removing outliers from the estimated values of the alveolar volume $V_A$ and/or pulmonary blood flow $\dot{Q}_P$, so as to give robust estimations of the alveolar volume $V_A$ and/or pulmonary blood flow $\dot{Q}_P$, and corresponding confidence intervals.

7. The method of claim 6, further comprising calculating the functional residual capacity as the sum of the alveolar volume $V_A$ and the dead space.

8. The method of claim 6, wherein the data used for the calculation of the alveolar volume $V_A$ and/or the pulmonary blood flow $\dot{Q}_P$ are obtained using a sinewave period in the range of 0.5 minutes to 5 minutes.

9. The method of claim 8, wherein the data used for the calculation of the alveolar volume $V_A$ and the pulmonary blood flow $\dot{Q}_P$ are obtained using a sinewave period of approximately 3 minutes.

10. The method of claim 9, wherein the period of the sinewave is varied across the range of 0.5 minutes to 5 minutes.

11. The method of claim 10, wherein periods in the range of 2 minutes to 4 minutes are used to determine inhomogeneity in respect of one or more of the alveolar volume $V_A$, functional residual capacity, and pulmonary blood flow $\dot{Q}_P$.

12. The method of claim 11, further comprising evaluating one or more of the following indices $I_1$, $I_2$, $I_3$ and $I_4$, wherein:

$$I_1 = \frac{V_A(4 \text{ mins}) - V_A(0.5 \text{ mins})}{V_A(0.5 \text{ mins})},$$

$$I_2 = \frac{V_{A,predict}}{V_A(0.5 \text{ mins})},$$

$$I_3 = \frac{V_{A,plethysmograph}}{V_A(0.5 \text{ mins})}, \text{ and}$$

$$I_4 = \frac{\dot{Q}_P(2 \text{ mins}) - \dot{Q}_P(4 \text{ mins})}{\dot{Q}_P(4 \text{ mins})};$$

in which $V_A$ (0.5 mins) and $V_A$ (4 mins) are the lung volume estimated at sinewave periods of 0.5 minutes and 4 minutes respectively; $\dot{Q}_P$ (2 mins) and $\dot{Q}_P$ (4 mins) are the pulmonary blood flow estimated at sinewave periods of 2 minutes and 4 minutes respectively, $V_{A,plethysmograph}$ is the lung volume measured by body plethysmography, and $V_{A,predict}$ is the predicted lung volume calculated from the height and weight of the subject.

13. The method of claim 12, wherein at least one of the fitting of the sinewave envelopes to the measured concentration values, and the calculating, is performed after the test has been carried out, and optionally without the patient being present.

14. A test apparatus configured for carrying out the method as claimed in claim 1.

15. A ventilator comprising the test apparatus as claimed in claim 14.

16. The method of claim 1 wherein adjusting ventilator settings in the ventilated patient in need thereof is a manual adjustment.

17. The method of claim 1 wherein adjusting ventilator settings in the ventilated patient in need thereof is carried out by a computer program which, when executed by a processor carries out, adjustment of the ventilator settings based on the result of said measurement of lung inhomogeneity.

18. The method of claim 17 wherein adjusting ventilator settings occurs automatically.

* * * * *